US008252296B2

(12) United States Patent
Chrisstoffels et al.

(10) Patent No.: US 8,252,296 B2
(45) Date of Patent: Aug. 28, 2012

(54) AQUEOUS POLYMER DISPERSION AND USE THEREOF IN COSMETICS

(75) Inventors: Lysander Chrisstoffels, Limburgerhof (DE); Peter Hössel, Schifferstadt (DE); Ivette Garcia Castro, Ludwigshafen Gartenstadt (DE); Claudia Wood, Weinheim (DE); Maximilian Angel, Schifferstadt (DE); Klemens Mathauer, Heidelberg (DE)

(73) Assignee: BASF SE, Ludwigshafen (DE)

( * ) Notice: Subject to any disclaimer, the term of this patent is extended or adjusted under 35 U.S.C. 154(b) by 1157 days.

(21) Appl. No.: 10/564,485

(22) PCT Filed: Jul. 13, 2004

(86) PCT No.: PCT/EP2004/007741
§ 371 (c)(1),
(2), (4) Date: Jan. 13, 2006

(87) PCT Pub. No.: WO2005/005497
PCT Pub. Date: Jan. 20, 2005

(65) Prior Publication Data
US 2006/0153793 A1    Jul. 13, 2006

(30) Foreign Application Priority Data
Jul. 14, 2003    (DE) ................. 103 31 865

(51) Int. Cl.
*A61K 8/04*        (2006.01)
*A61K 8/81*        (2006.01)
*C08F 26/00*       (2006.01)
*C08F 226/02*      (2006.01)
*C08F 226/06*      (2006.01)

(52) U.S. Cl. ......... 424/401; 526/258; 526/264; 526/312
(58) Field of Classification Search ................. None
See application file for complete search history.

(56) References Cited

U.S. PATENT DOCUMENTS

| 5,134,187 | A  | * | 7/1992  | Aihara .......................... 524/548 |
| 5,840,804 | A  |   | 11/1998 | Carl et al. |
| 6,174,950 | B1 |   | 1/2001  | Nzudie et al. |
| 6,231,876 | B1 |   | 5/2001  | Niessner et al. |
| 6,362,245 | B1 |   | 3/2002  | Takahashi et al. |
| 6,426,383 | B1 |   | 7/2002  | Fong et al. |
| 6,682,725 | B1 | * | 1/2004  | Dieing et al. .............. 424/70.11 |
| 7,125,926 | B2 | * | 10/2006 | Satoh et al. .................... 524/502 |
| 7,422,735 | B1 | * | 9/2008  | Hossel et al. .............. 424/70.15 |
| 2001/0021375 | A1 | * | 9/2001 | Hossel et al. .................. 424/59 |
| 2003/0091602 | A1 |   | 5/2003 | Witteler et al. |
| 2003/0147929 | A1 | * | 8/2003 | Kim et al. ..................... 424/401 |
| 2005/0175572 | A1 |   | 8/2005 | Nguyen-Kim et al. |
| 2005/0265950 | A1 | * | 12/2005 | Chrisstoffels et al. ..... 424/70.17 |
| 2005/0281774 | A1 | * | 12/2005 | Muller et al. .............. 424/70.15 |
| 2006/0183822 | A1 | * | 8/2006 | Nguyen-Kim et al. ......... 524/35 |

FOREIGN PATENT DOCUMENTS

| DE | 19851024 A1 | 11/1998 |
| DE | 10237378 A1 | 8/2002 |
| DE | 10261197 A1 | 12/2002 |
| DE | 10261750 A1 | 12/2002 |
| EP | 0 183 466 A2 | 6/1986 |
| FR | 2815635 A1 | 10/2000 |
| FR | 2816833 A1 | 11/2000 |
| WO | WO-98/54234 A1 | 12/1998 |
| WO | WO 0162809 A1 * | 8/2001 |
| WO | WO 2004022616 A1 * | 3/2004 |
| WO | WO 2004030642 A1 * | 4/2004 |

* cited by examiner

*Primary Examiner* — Ernst Arnold
*Assistant Examiner* — Christopher R Lea
(74) *Attorney, Agent, or Firm* — Connolly Bove Lodge & Hutz LLP

(57) ABSTRACT

The present invention relates to an aqueous polymer dispersion which is obtainable by free-radical polymerization of a monomer mixture which comprises at least one amide-group-containing compound, at least one crosslinker and at least one monomer with at least one cationogenic and/or cationic group. The invention further relates to the polymers obtainable by drying such a polymer dispersion, and to cosmetic or pharmaceutical compositions which comprise such a polymer dispersion or such a polymer.

20 Claims, No Drawings

AQUEOUS POLYMER DISPERSION AND USE THEREOF IN COSMETICS

This application is a National Stage of PCT/EP2004/007741 filed Jul. 13, 2004 which in turn claims priority from German Application 103 31 865.8 filed Jul. 14, 2003.

The present invention relates to an aqueous polymer dispersion which is obtainable by free-radical polymerization of a monomer mixture which comprises at least one amide-group-containing compound, at least one crosslinker and at least one monomer with at least one cationogenic and/or cationic group. The invention further relates to the polymers obtainable by drying such a polymer dispersion, and to cosmetic or pharmaceutical compositions which comprise such a polymer dispersion or such a polymer.

Cosmetically and pharmaceutically acceptable water-soluble polymers are used widely in cosmetics and medicine. In soaps, creams and lotions, for example, they are usually used as formulation agents, e.g. as thickener, foam stabilizer or water absorbent, or else to alleviate the irritative effect of other ingredients or to improve the dermal application of active ingredients. Their task in hair cosmetics is to influence the properties of the hair. In pharmacy, they are used, for example, as coatings or binders for solid drug forms.

For hair cosmetics, film-forming polymers are used, for example, as conditioners in order to improve the dry and wet combability, the feel to the touch, shine and appearance, and to impart antistatic properties to the hair. It is known to use water-soluble polymers with cationic functionalities in hair conditioners which have a greater affinity to the surface of the hair, which is negatively charged as a consequence of its structure, and prevent electrostatic charging of the hair. The structure and mode of action of various hair treatment polymers are described in Cosmetic & Toiletries 103 (1988) 23. Standard commercial cationic conditioning polymers are e.g. cationic hydroxyethylcellulose, cationic polymers based on N-vinylpyrrolidone, e.g. copolymers of N-vinylpyrrolidone and quaternized N-vinylimidazole or copolymers of acrylamide and diallyldimethylammonium chloride. The latter have the disadvantage in this case of a high residual monomer content since the copolymerization parameters of these monomers are unfavorable.

To set hairstyles, use is made, for example, of vinyllactam homo- and copolymers and carboxylate-group-containing polymers. Requirements for hair-setting resins are, for example, strong hold at high atmospheric humidity, elasticity, ability to be washed out of the hair, compatibility in the formulation and a pleasant feel of the hair treated therewith.

It is often problematical to provide products with a complex profile of properties. Thus, there is a need for polymers for cosmetic compositions which are able to form essentially smooth, tack-free films which give the hair and the skin good sensorily ascertainable properties, such as a pleasant feel, and at the same time have a good conditioning effect or setting effect. In addition to good cosmetic effect properties, it should be possible to formulate products with the highest possible solids contents coupled with good rheological properties. In addition, esthetic requirements are increasingly placed by the consumer on cosmetic and pharmaceutical products. Thus, in the case of products of this type, a preference for clear, opaque formulations is currently being observed. For this purpose, the polymers used must have good compatibility with as many of the other cosmetic formulation constituents as possible.

EP-A-183 466 describes a process for the preparation of a polymer dispersion by polymerization of a water-soluble monomer in an aqueous salt-containing medium in the presence of a dispersant. The water-soluble monomer may, inter alia, be an ethylenically unsaturated compound with a cationic group. Dispersants which may be used are polyelectrolytes whose ionogenic/ionic groups have to correspond to the charge of the monomers used. A co-use of crosslinkers during the polymerization is not described.

EP-A-670 333 describes crosslinked water-soluble polymer dispersions which are obtainable by polymerization of a monomer mixture comprising at least one water-soluble monomer, at least one crosslinker, and optionally hydrophobic and/or amphiphilic monomers in the presence of a polymeric dispersant. As well as a large number of others, water-soluble monomers which may be used are also N-vinylpyrrolidone and monomers with cationic/cationizable groups, such as N-vinylimidazole. The polymeric dispersants may be polyelectrolytes which contain, in copolymerized form, for example salts of (meth)acrylic acid as anionic monomer building blocks or quaternized derivatives of N,N-dimethylaminoethyl(meth)acrylate as cationic building blocks. This document specifically describes neither the use of monomer mixtures which comprise an amide-group-containing monomer, a crosslinker and a monomer with cationogenic/cationic groups, nor the use of monomer mixtures and dispersants with oppositely charged/chargeable groups.

EP-A-855 407 describes compositions based on water-soluble polymers which are obtainable by polymerization of at least one water-soluble monomer in the presence of a styrene-maleic anhydride copolymer. The water-soluble monomers used may, inter alia, be ethylenically unsaturated compounds with cationogenic/cationic groups. The application further relates to water-soluble compositions which comprise at least one water-soluble polymer and a polymeric dispersant and where the water-soluble polymer contains, in copolymerized form, a cationic acrylic monomer with a benzylammonium group. The dispersants of the last-mentioned compositions may also be poly(diallyldimethylammonium chloride), as well as styrene-maleic anhydride copolymers. Polymers which contain, in copolymerized form, at least one N-vinylamide-group-containing compound and at least one crosslinker are not described.

WO 98/54234 describes aqueous dispersions of polymers which contain, in copolymerized form, an N-vinylamide monomer, and optionally further comonomers. These comonomers may, for example, be vinylpyrrolidone or acrylate monomers with cationogenic/cationic groups. The preparation takes place by polymerization in the presence of a water-soluble stabilizer polymer. Suitable stabilizer polymers mentioned are poly(dimethylaminoethyl acrylate) quaternized with methyl chloride, and polyvinyl alcohol. Aqueous polymer dispersions which are obtainable, by free-radical polymerization of a monomer mixture which comprises at least one cationic monomer and at least one crosslinker, in the presence of an anionic dispersant are not described.

A use of the polymers and polymer dispersions described in the abovementioned documents in cosmetics is not described.

EP-A-929 285 teaches the use of water-soluble copolymers which contain, in copolymerized form, vinylcarboxamide units and vinylimidazole units as a constituent of cosmetic compositions. The use of crosslinkers for modifying these polymers is also described. The polymerization in the presence of at least one polymeric anionic dispersant, by contrast, is not disclosed in this document.

WO 00/27893 describes aqueous polymer dispersions based on N-vinylcarboxamides and optionally further comonomers, where the polymerization takes place in the presence of at least one polymeric dispersant. A use in cosmetics is described only very generally and without demonstration by a working example.

WO 02/34796 describes a polymerization process in which at least one monomer is fractionally polymerized in the presence of at least one water-soluble polymeric dispersant and a salt mixture. The monomers may be water-soluble nonionic, anionic or cationic monomers. Polymeric dispersants which may be used are polyelectrolytes, where the dispersants have the same charge as the monomers used for the polymerization. A use of these polymers in cosmetics is described only very generally without indication of a possible field of use.

WO 02/41856 describes the use of polymer dispersions, which are obtainable by polymerization of at least one water-soluble monomer in an aqueous salt solution which comprises at least one polyelectrolyte as dispersant, for the cosmetic treatment of keratin materials. In addition, the dispersions comprise at least one agent for adjusting the viscosity, for example a polycarboxylic acid or a salt thereof. Water-soluble monomers which may be use are cationic, anionic and nonionic monomers, preference being given to monomer mixtures which comprise at least one cationic monomer, and optionally additionally acrylic acid and/or acrylamide. Only cationic polyelectrolytes are specifically disclosed as suitable dispersants. The preparation of the polymer dispersions in the presence of at least one crosslinker is not described.

The unpublished international application PCT/EP03/04647 describes cosmetic or pharmaceutical compositions which comprise at least one water-soluble or water-dispersible copolymer which is obtainable by free-radical copolymerization of a monomer mixture comprising (meth)acrylamide, at least one amide-group-containing monomer and optionally further compounds copolymerizable therewith. Crosslinkers may also be used as further monomers.

The unpublished German patent application P 102 61 750.3 describes an ampholytic copolymer which is obtainable by free-radical copolymerization of
a) at least one ethylenically unsaturated compound with at least one anionogenic and/or anionic group,
b) at least one ethylenically unsaturated compound with at least one cationogenic and/or cationic group,
c) at least one unsaturated amide-group-containing compound
and optionally further comonomers. Crosslinkers may also be used to prepare these ampholytic copolymers. Also described are polyelectrolyte complexes which contain such an ampholytic copolymer, and also cosmetic or pharmaceutical compositions based on these ampholytic copolymers and polyelectrolyte complexes.

The unpublished German patent application 102 37 378.7 describes the use of polymers obtainable by
(i) free-radically initiated copolymerization of monomer mixtures of
  (a) at least one cationic monomer or quaternizable monomer,
  (b) optionally a water-soluble monomer,
  (c) optionally a further free-radically copolymerizable monomer,
  (d) at least one monomer effective as crosslinker and having at least two ethylenically unsaturated, nonconjugated double bonds, and
  (e) at least one regulator,
(ii) subsequent quaternization or protonation of the polymer if the monomer (a) used is an unquaternized or only partially quaternized monomer,
in hair cosmetic preparations.

The unpublished German patent application 102 61 197.1 describes an aqueous dispersion obtainable by free-radical polymerization of
a) at least one N-vinyl-containing monomer,
b) at least one polymeric dispersant,
c) at least one polymeric precipitation agent,
d) at least one crosslinker,
e) optionally further monomers,
f) optionally at least one regulator,
g) optionally a buffer substance,
where the weight ratio of b) to c) is in the range from 1:50 to 1:0.02, and to the use thereof in cosmetic preparations.

Despite extensive efforts, there is still a need to improve the polymers known from the prior art for producing elastic hairstyles coupled with strong hold, even at high atmospheric humidity, good ability to be washed out and good feel of the hair. The need for improvement likewise exists for polymers for producing readily combable, detangleable hair and for conditioning skin and hair with regard to their sensorily ascertainable properties, such as feel, volume, handleability, etc. Also desirable are clear aqueous preparations of these polymers which are accordingly characterized by good compatibility with other formulation constituents.

There is also a need for polymers which are suitable as conditioners for cosmetic preparations and which can be prepared with a high solids content. Of particular interest are polymers which have a high solids content, have a low viscosity coupled with good performance properties (such as, for example, combability).

It is an object of the present invention to find a conditioning agent for cosmetic preparations, in particular shampoos, which does not have the stated disadvantages.

We have found that this object is achieved by aqueous polymer dispersions and the polymers obtainable therefrom by drying, which are obtainable by free-radical polymerization of a monomer mixture comprising at least one N-vinyl-containing monomer, at least one crosslinker and at least one monomer with at least one cationogenic and/or cationic group in an aqueous medium in the presence of at least one polymeric anionic dispersant.

The invention therefore provides an aqueous polymer dispersion Pd) which is obtainable by free-radical polymerization of a monomer mixture M) comprising
a) at least one α,β-ethylenically unsaturated amide-group-containing compound of the formula I

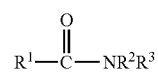

(I)

where
  $R^2$ is a group of the formula $CH_2\!=\!CR^4\!-$ and $R^1$ and $R^3$, independently of one another, are H, alkyl, cycloalkyl, heterocycloalkyl, aryl or hetaryl, or $R^1$ and $R^3$, together with the amide group to which they are bonded, are a lactam with 5 to 8 ring atoms,
b) at least one free-radically polymerizable crosslinking compound with at least two α,β-ethylenically unsaturated double bonds per molecule,
c) at least one compound with a free-radically polymerizable α,β-ethylenically unsaturated double bond and at least one cationogenic and/or cationic group per molecule,
in an aqueous medium in the presence of at least one polymeric anionic dispersant D).

The invention further provides a polymer P) obtainable by drying a polymer dispersion Pd), cosmetic or pharmaceutical compositions which comprise such a polymer dispersion or such a polymer, and the use of these polymer dispersions and polymers.

For the purposes of the present invention, the term alkyl includes straight-chain and branched alkyl groups. Suitable short-chain alkyl groups are e.g. straight-chain or branched $C_1$-$C_7$-alkyl, preferably $C_1$-$C_6$-alkyl and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

Suitable longer-chain $C_8$-$C_{30}$-alkyl or $C_8$-$C_{30}$-alkenyl groups are straight-chain and branched alkyl or alkenyl groups. Preference is given here to predominantly linear alkyl radicals, as arise also in natural or synthetic fatty acids and fatty alcohols, and oxo alcohols, which may optionally be additionally mono-, di- or polyunsaturated. These include e.g. n-hexyl(ene), n-heptyl(ene), n-octyl(ene), n-nonyl(ene), n-decyl(ene), n-undecyl(ene), n-dodecyl(ene), n-tridecyl (ene), n-tetradecyl(ene), n-pentadecyl(ene), n-hexadecyl (ene), n-heptadecyl(ene), n-octadecyl(ene), n-nonadecyl (ene) etc.

Cycloalkyl is preferably $C_5$-$C_8$-cycloalkyl, such as cyclopentyl, cyclohexyl, cycloheptyl or cyclooctyl.

Aryl includes unsubstituted and substituted aryl groups and is preferably phenyl, tolyl, xylyl, mesityl, naphthyl, fluorenyl, anthracenyl, phenanthrenyl, naphthacenyl and in particular is phenyl, tolyl, xylyl or mesityl.

In the text below, compounds which may be derived from acrylic acid and methacrylic acid are sometimes referred to in abbreviated form by adding the syllable "(meth)" to the compound derived from acrylic acid.

The polymer dispersions Pd) and polymers P) according to the invention are suitable, inter alia, for formulating gels. "Gel-like consistency" is exhibited by formulations which have a higher viscosity than a liquid and which are self-supporting, i.e. they retain a shape given to them without shape-stabilizing covering. In contrast to solid formulations, however, gel-like formulations can be readily deformed under the application of shear forces. The viscosity of the gel-like compositions is preferably in a range greater than 600 to about 60 000 mPas, particularly preferably from 6 000 to 30 000 mPas. The gels are preferably hair gels.

For the purposes of the present invention, water-soluble monomers and polymers are understood as meaning monomers and polymers which dissolve in water in an amount of at least 1 g/l at 20° C. Water-dispersible monomers and polymers are understood as meaning monomers and polymers which disintegrate into dispersible particles under the application of shear forces, for example by stirring. Hydrophilic monomers are preferably water-soluble or at least water-dispersible. The polymers P) according to the invention are generally redispersible or soluble in aqueous media.

The monomer mixture M) used to prepare the polymer dispersions Pd) according to the invention has monomers with cationogenic and/or cationic groups. In a suitable embodiment, monomers with anionogenic and/or anionic groups can also additionally be used for the polymerization.

The amount of monomers with anionogenic and/or anionic groups used for the polymerization is such that, based on the monomers used overall for the polymerization, the molar fraction of anionogenic and anionic groups is less than the molar fraction of cationogenic and cationic groups. The polymers P) present in the aqueous polymer dispersions Pd) therefore have on average a molar excess of cationogenic/cationic groups compared with anionogenic/anionic groups.

To prepare the aqueous polymer dispersions according to the invention, use is preferably made of monomers with charged, i.e. with cationic, groups. It is, however, also possible to use these monomers in partially or completely non-protonated and quaternized form. If, for the preparation of the dispersions Pd), both monomers with cationogenic/cationic groups and also monomers with anionogenic/anionic groups are used, then these may be used either in uncharged form or else in charged form. In a suitable embodiment, these monomers are used together, i.e. in the form of "salt pairs". If already charged monomers are used for the preparation, then their counterions are preferably derived from acids or bases, as are described below for adjusting the pH during the polymerization or of the resulting polymers.

The polymeric anionic dispersants D) are polyelectrolytes with a relatively large number of anionically dissociatable groups in the main chain and/or a side chain. For the polymerization, the dispersants D) may be used in essentially uncharged form or in partially or completely charged form. The counterions which the charged groups of the anionic dispersants carry are preferably derived from bases, as described below for adjusting the pH during the polymerization. The polymeric anionic dispersants D) used according to the invention are able to form polyelectrolyte complexes (symplexes) with the polymers P) present in the dispersions Pd).

For the polymerization, the pH of the aqueous medium is generally adjusted to a value of from 5 to 10, preferably 6 to 8, particularly preferably 6.5 to 7.5 and in particular 6.8 to 7. It is advantageous to maintain the pH in the abovementioned ranges during the polymerization. In many cases, the addition of pH-regulating substances, such as acids, bases or buffers, to the polymerization mixture is not necessary since the combination of monomers with cationogenic/cationic groups used according to the invention and dispersants with anionogenic/anionic groups already act as buffers, and the pH values of the aqueous polymerization medium are stable within a wide range toward dilution and the addition of acid or base. In a suitable embodiment, however, it is also possible to add a buffer to the polymerization. Suitable buffer mixtures are described, for example, in Römpp, Chemielexikon, 9$^{th}$ edition, Paperback edition, Volume 5, pp. 3677-3678, Verlag Thieme (1995), which is hereby incorporated by reference. Furthermore, it is also possible to determine the pH of the polymerization mixture during the polymerization, for example using a combination electrode, and to keep it in the preferred pH range by adding acid or base.

To adjust the pH during the polymerization or after it, all inorganic or organic acids and bases are in principle suitable, in particular those which are water-soluble. Suitable acids are e.g. carboxylic acids, such as lactic acid, citric acid or tartaric acid or mineral acids, such as phosphoric acid, sulfuric acid or hydrochloric acid. Suitable bases are e.g. alkali metal and alkaline earth metal hydroxides, ammonia, and primary, secondary and tertiary amines, such as triethylamine, and amino alcohols, such as triethanolamine, methyldiethanolamine, dimethylethanolamine or 2-amino-2-methylpropanol. Suitable buffers are preferably salts of the abovementioned weak acids, preferably alkali metal and alkaline earth metal salts, such as sodium, potassium, ammonium or magnesium salts. Preferred buffer substances are sodium acetate, sodium citrate, sodium pyrophosphate, potassium pyrophosphate, sodium dihydrogenphosphate, disodium hydrogenphosphate, sodium hydrogencarbonate and/or sodium borate. Said pH-adjusting substances may be used either individually or else in mixtures. The buffer substances may be added to adjust the pH together or else in each case individually.

The preparation of crosslinked cationic polymers by conventional polymerization processes, e.g. by solution or bulk polymerization, generally leads to high molecular weight polymeric networks whose performance properties are still in need of improvement with regard to use in cosmetic and pharmaceutical compositions. Thus, polymer compositions generally result here in which the polymers are present in dissolved or swollen form and which have very high viscosities. The preparation process used according to the invention gives polymer dispersions, i.e. polymer compositions which are characterized by a relatively large proportion of dispersed discrete particles present therein. It is assumed that the crosslinking also only takes place here partly within the dispersion particles, meaning that the resulting dispersions have higher solids contents and lower viscosities than the crosslinked cationic polymer compositions known from the prior art. In terms of performance, they are characterized, for example, by improved effectiveness as conditioners. They also generally have good rheological properties, which are independent in wide ranges of the degree of crosslinking (proportion of component b)).

A determination as to what extent the polymers are present in polymer compositions in the form of dispersed discrete particles or in dissolved or swollen form can take place by means of turbidity measurement (turbidimetry). Dispersed discrete particles scatter incident light more considerably than do dissolved or swollen polymer particles. For the measurement, the radiated scattered light or fluorescent radiation proportion or in the simplest case the absorbance of the transmitted light can be used.

The dispersions obtainable according to the invention have, in a preferred embodiment, an LT value of less or equal to 30%, in particular less than or equal to 20%, preferably less than or equal to 10%, in particular less than or equal to 5%.

The determination of the LT value (light transmittance) for aqueous polymer dispersions is measured e.g. relative to pure water as reference with a cell length of 2.5 cm at 600 nm. The spectrophotometer (e.g. Hach: Spectrophotometer DR/2000, measurement method "transmission") is firstly adjusted to 100% with pure water. The cell is then rinsed a number of times with the dispersion, the dispersion is poured into the cell and the light transmittance is read off in %.

The polymerization medium can consist either only of water or else of mixtures of water and water-miscible liquids, e.g. alcohols, such as e.g. methanol, ethanol, n-propanol, isopropanol etc. Preference is given to using only water.

Monomer a)

Suitable monomers a) are N-vinyllactams and derivatives thereof, which may have e.g. one or more $C_1$-$C_6$-alkyl substituents, such as methyl, ethyl, n-propyl, isopropyl, n-butyl, sec-butyl, tert-butyl etc. These include e.g. N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. Preference is given to using N-vinylpyrrolidone and N-vinylcaprolactam.

Open-chain N-vinylamide compounds suitable as monomers a) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide.

In a preferred embodiment of the invention, an N-vinyllactam, in particular N-vinylpyrrolidone, is used as monomer a).

Crosslinker b)

Monomers b) which have a crosslinking function are compounds with at least two ethylenically unsaturated, nonconjugated double bonds in the molecule.

Suitable crosslinkers b) are, for example, acrylic esters, methacrylic esters, allylethers or vinylethers of at least dihydric alcohols. The OH groups of the parent alcohols may here be completely or partially etherified or esterified; however, the crosslinkers contain at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis (hydroxymethyl)-cyclohexane, hydroxypivalic neopentyl glycol monoester, 2,2-bis(4-hydroxyphenyl)-propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1, 5-diol, and polyethylene glycols, polypropylene glycols and polytetrahydrofurans with molecular weights of in each case 200 to 10 000. Apart from the homopolymers of ethylene oxide or propylene oxide, it is also possible to use block copolymers of ethylene oxide or propylene oxide or copolymers which contain ethylene oxide and propylene oxide groups in incorporated form. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. The polyhydric alcohols can of course also be used following reaction with ethylene oxide or propylene oxide, in the form of the corresponding ethoxylates or propoxylates, respectively. The polyhydric alcohols can also firstly be converted into the corresponding glycidyl ethers by reaction with epichlorohydrin.

Further suitable crosslinkers b) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers b) are esters of unsaturated carboxylic acids with the above-described polyhydric alcohols, for example of oleic acid, crotonic acid, cinnamic acid or 10-undecenoic acid.

Suitable monomers b) are also straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Further suitable crosslinkers are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable are triallylamine and triallylmonoalkylammonium salts, e.g. triallylmethylammonium chloride or methylsulfate, as crosslinker b).

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropylene urea.

Further suitable crosslinkers are divinyldioxane, tetraallylsilane or tetravinylsilane.

It is of course also possible to use mixtures of the abovementioned compounds. Preference is given to using water-soluble crosslinkers.

Particularly preferably used crosslinkers b) are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

As crosslinker b), very particular preference is given to pentaerythritol triallyl ether, methylenebisacrylamide, N,N'-divinylethyleneurea, triallylamine and triallylmonoalkylammonium salt and acrylic esters of glycol, butanediol, trimethylolpropane or glycerol or acrylic esters of glycol, butanediol, trimethylolpropane or glycerol reacted with ethylene oxide and/or epichlorohydrin.

Monomer c)

The cationogenic or cationic groups of component c) are preferably nitrogen-containing groups, such as primary, secondary and tertiary amino groups, and quaternary ammonium groups. The nitrogen-containing groups are preferably tertiary amino groups or quaternary ammonium groups. Charged cationic groups can be produced from the amine nitrogens either by protonation, e.g. with monobasic or polybasic carboxylic acids, such as lactic acid or tartaric acid, or mineral acids, such as phosphoric acid, sulfuric acid and hydrochloric acid, or by quaternization, e.g. with alkylating agents, such as $C_1$-$C_4$-alkyl halides or sulfates. Examples of such alkylating agents are ethyl chloride, ethyl bromide, methyl chloride, methyl bromide, dimethyl sulfate and diethyl sulfate. In a preferred embodiment, the monomers c) are used in charged form for the polymerization.

Suitable compounds c) are e.g. the esters of α,β-ethylenically unsaturated mono- and dicarboxylic acids with aminoalcohols. Preferred aminoalcohols are $C_2$-$C_{12}$-aminoalcohols which are $C_1$-$C_8$-dialkylated on the amine nitrogen. Suitable acid components of these esters are e.g. acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof. Preference is given to N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate and N,N-dimethylaminocyclohexyl(meth)acrylate.

Suitable monomers c) are also the amides of the abovementioned α,β-ethylenically unsaturated mono- and dicarboxylic acids with diamines which have at least one primary or secondary amino group. Preference is given to diamines which have a tertiary and a primary or secondary amino group. Preferred monomers c) are N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamid, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide etc. Particular preference is given to using N-[3-(dimethylamino)propyl]acrylamide and/or N-[3-(dimethylamino)propyl]methacrylamide.

Further suitable monomers c) are N,N-diallylamines and N,N-diallyl-N-alkylamines and acid addition salts and quaternization products thereof. Alkyl here is preferably $C_1$-$C_{24}$-alkyl. Preference is given to N,N-diallyl-N-methylamine and N,N-diallyl-N,N-dimethylammonium compounds, such as e.g. the chlorides and bromides.

Suitable monomers c) are also vinyl- and allyl-substituted nitrogen heterocycles, such as N-vinylimidazole, N-vinyl-2-methylimidazole, vinyl- and allyl-substituted heteroaromatic compounds, such as 2- and 4-vinylpyridine, 2- and 4-allylpyridine, and the salts thereof.

Preferred monomers c) are the N-vinylimidazole derivatives of the formula (II) in which $R^1$ to $R^3$ is hydrogen, $C_1$-$C_4$-alkyl or phenyl

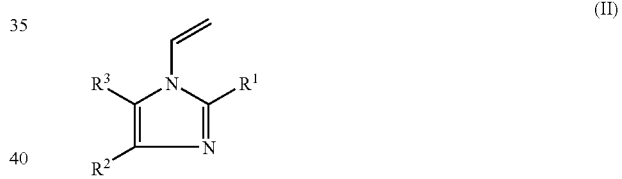

(II)

Examples of compounds of the formula (II) are given in Table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

Preferred examples of monomers c) are 3-methyl-1-vinylimidazolium chloride and methosulfate, dimethyldiallylammonium chloride, and N,N-dimethylaminoethyl methacrylate and N-[3-(dimethylamino)propyl]methacrylamide, which have been quaternized by methyl chloride, dimethyl sulfate or diethyl sulfate.

Particularly preferred monomers c) are 3-methyl-1-vinylimidazolium chloride and methosulfate and dimethyldiallylammonium chloride (DADMAC), and very particular preference is given to 3-methyl-1-vinylimidazolium chloride and methosulfate.

A preferred combination of components a) and c) includes at least one N-vinyllactam, in particular N-vinylpyrrolidone, and at least one N-vinylimidazole derivative, in particular a quaternized vinylimidazole, and/or diallyldimethylammonium chloride.

Monomer d)

The monomer mixtures M) used to prepare the polymer dispersions Pd) can additionally comprise at least one further monomer d). The additional monomers d) are preferably chosen from esters of $\alpha,\beta$-ethylenically unsaturated mono- and dicarboxylic acids, with $C_1$-$C_{30}$-alkanoles and $C_1$-$C_{30}$-alkanediols, amides of $\alpha,\beta$-ethylenically unsaturated mono- and dicarboxylic acids with $C_2$-$C_{30}$-aminoalcohols, which have a primary or secondary amino group, primary amides of $\alpha,\beta$-ethylenically unsaturated monocarboxylic acids and N-alkyl and N,N-dialkyl derivatives thereof, esters of vinyl alcohol and allyl alcohol with $C_1$-$C_{30}$-monocarboxylic acids, vinyl ethers, vinyl aromatics, vinyl halides, vinylidene halides, $C_1$-$C_8$-monoolefins, nonaromatic hydrocarbons with at least two conjugated double bonds and mixtures thereof.

Suitable additional monomers d) are methyl(meth)acrylate, methyl ethacrylate, ethyl(meth)acrylate, ethyl ethacrylate, tert-butyl(meth)acrylate, tert-butyl ethacrylate, n-octyl (meth)acrylate, 1,1,3,3-tetramethylbutyl(meth)acrylate, ethylhexyl(meth)acrylate, n-nonyl(meth)acrylate, n-decyl (meth)acrylate, n-undecyl(meth)acrylate, tridecyl(meth) acrylate, myristyl(meth)acrylate, pentadecyl(meth)acrylate, palmityl(meth)acrylate, heptadecyl(meth)acrylate, nonadecyl(meth)acrylate, arachidyl(meth)acrylate, behenyl(meth) acrylate, lignoceryl(meth)acrylate, cerotinyl(meth)acrylate, melissinyl(meth)acrylate, palmitoleinyl(meth)acrylate, oleyl (meth)acrylate, linolyl(meth)acrylate, linolenyl(meth)acrylate, stearyl(meth)acrylate, lauryl(meth)acrylate and mixtures thereof.

Suitable additional monomers d) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc.

Suitable additional monomers d) are also acrylamide, methacrylamide, N-methyl(meth)acrylamide, N-ethyl(meth) acrylamide, N-propyl(meth)acrylamide, N-(n-butyl)(meth) acrylamide, N-(tert-butyl)(meth)acrylamide, N-(n-octyl) (meth)acrylamide, N-(1,1,3,3-tetramethylbutyl)(meth) acrylamide, N-ethylhexyl(meth)acrylamide, N-(n-nonyl) (meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth) acrylamide, N-nonadecyl(meth)acrylamide, N-arachidyl (meth)acrylamide, N-behenyl(meth)acrylamide, N-lignoceryl(meth)acrylamide, N-cerotinyl(meth)acrylamide, N-melissinyl(meth)acrylamide, N-palmitoleinyl (meth)acrylamide, N-oleyl(meth)acrylamide, N-linolyl (meth)acrylamide, N-linolenyl(meth)acrylamide, N-stearyl (meth)acrylamide, N-lauryl(meth)acrylamide, N,N-dimethyl (meth)acrylamide, N,N-diethyl(meth)acrylamide, morpholinyl(meth)acrylamide.

Suitable additional monomers d) are also vinyl acetate, vinyl propionate, vinyl butyrate and mixtures thereof.

Suitable additional monomers d) are also ethylene, propylene, isobutylene, butadiene, styrene, $\alpha$-methylstyrene, acrylonitrile, methacrylonitrile, vinyl chloride, vinylidene chloride, vinyl fluoride, vinylidene fluoride and mixtures thereof.

The above-mentioned additional monomers d) may be used individually or in the form of any desired mixtures.

Monomer e)

The monomer mixture M) may additionally comprise at least one compound e) with a free-radically polymerizable $\alpha,\beta$-ethylenically unsaturated double bond and with an anionogenic and/or anionic group per molecule, with the proviso that the molar proportion of anionogenic and anionic groups in component e) is less than the molar proportion of cationogenic and cationic groups in component c).

The compounds e) are preferably chosen from monoethylenically unsaturated carboxylic acids, sulfonic acids, phosphonic acids and mixtures thereof.

The monomers e) include monoethylenically unsaturated mono- and dicarboxylic acids having 3 to 25, preferably 3 to 6, carbon atoms, which may also be used in the form of their salts or anhydrides. Examples thereof are acrylic acid, methacrylic acid, ethacrylic acid, a-chloroacrylic acid, crotonic acid, maleic acid, maleic anhydride, itaconic acid, citraconic acid, mesaconic acid, glutaconic acid, aconitic acid and fumaric acid. The monomers e) further include the half-esters of monoethylenically unsaturated dicarboxylic acids having 4 to 10, preferably 4 to 6, carbon atoms, e.g. of maleic acid, such as monomethyl maleate. The monomers e) also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid and allylphosphonic acid. The monomers e) also include the salts of the abovementioned acids, in particular the sodium, potassium and ammonium salts, and also the salts with the abovementioned amines. The monomers e) may also be used as they are or as mixtures. The given proportions by weight all refer to the acid form.

Component e) is preferably chosen from acrylic acid, methacrylic acid, ethacrylic acid, $\alpha$-chloroacrylic acid, crotonic acid, maleic acid, maleic anhydride, fumaric acid, itaconic acid, citraconic acid, mesaconic acid, glutaconic acid, aconitic acid and mixtures thereof.

Component e) is particularly preferably chosen from acrylic acid, methacrylic acid, itaconic acid and mixtures thereof.

Dispersant D)

To prepare the aqueous polymer dispersions Pd) according to the invention, use is made of a polymeric anionic dispersant D) which serves to disperse the polymers obtained during the free-radical polymerization of the monomer mixture M).

The number-average molecular weight of the dispersant D) is preferably in a range from 500 to 2 000 000, particularly preferably 1 000 to 100 000, in particular from 5 000 to 90 000 and specifically from 10 000 to 700 000.

Suitable dispersants D) are obtainable e.g. by free-radical polymerization of $\alpha,\beta$-ethylenically unsaturated monomers. In this connection, use is made of monomers which have at least one free-radically polymerizable, $\alpha,\beta$-ethylenically unsaturated double bond and at least one anionogenic and/or anionic group per molecule. For the preparation of the dispersant D) it is possible to use the abovementioned monomers e), which are hereby incorporated in their enterity by reference.

Preferred polymeric dispersants D) are polymers which contain, in copolymerized form, at least 5% by weight, particularly preferably at least 10% by weight and in particular at least 30% by weight, of at least one monomer with a free-radically polymerizable $\alpha,\beta$-ethylenically unsaturated double bond and an anionogenic and/or anionic group per molecule, based on the total weight of the monomers used for the preparation of the dispersants D).

In principle, suitable comonomers for the preparation of the dispersants D) are the components a) to d) specified above as components of the monomer mixture M) with the proviso that the molar proportion of anionogenic and anionic groups which the dispersant D) contains in copolymerized form is greater than the molar proportion of cationogenic and cationic groups. The polymeric anionic dispersants D) always differ in this respect from the polymers obtained by free-radical polymerization of the monomer mixture M).

The anionic dispersant D) is preferably chosen from polymers which contain, in copolymerized form, at least one monomer chosen from acrylic acid, methacrylic acid, maleic acid and mixtures thereof.

The acid groups of the dispersants D) may be partially or completely neutralized. At least some of the acid groups are then in deprotonated form, the counterions preferably being chosen from alkali metal ions, such as $Na^+$, $K^+$, ammonium ions, and organic derivatives thereof etc.

Preferred dispersants D) are e.g. maleic acid-acrylic acid copolymers and salts thereof (e.g. Sokalan® CP 5 from BASF Aktienges.), maleic acid-alkyl vinyl ether copolymers, such as, for example, maleic acid/methyl vinyl ether copolymers and salts thereof (e.g. Sokalan® CP 2), maleic acid-olefin copolymers and salts thereof (e.g. Sokalan® CP 9), poly-acrylic acid and salts thereof (e.g. Sokalan® CP 10), maleic anhydride-styrene copolymers, etc.

These polymeric dispersants are prepared by known processes, for example of solution, precipitation, suspension or emulsion polymerization using compounds which form free radicals under the polymerization conditions. The polymerization temperatures are usually in the range from 30 to 200° C., preferably 40 to 110° C. Suitable initiators are, for example, azo and peroxy compounds, and the customary redox initiator systems, such as combinations of hydrogen peroxide and compounds with a reducing effect, e.g. sodium sulfite, sodium bisulfite, sodium formaldehyde sulfoxylate and hydrazine. These systems may optionally additionally also comprise small amounts of a heavy metal salt.

Use Amounts of the Components

To prepare the aqueous polymer dispersions Pd) according to the invention, component a) is preferably used in an amount of from 10 to 90% by weight, preferably 20 to 70% by weight, in particular 30 to 60% by weight, based on the total weight of component a) and the dispersant D).

The dispersant D) is preferably used in an amount of from 10 to 90% by weight, preferably 20 to 70% by weight, in particular 30 to 60% by weight, based on the total weight of component a) and the dispersant D).

Component d) is preferably used in an amount of from 0.0005 to 5% by weight, preferably 0.001 to 2.5% by weight, in particular 0.01 to 1.5% by weight, based on the weight of component a).

For the preparation of the aqueous polymer dispersion Pd) according to the invention, component c) is preferably used in an amount of from 1 to 40% by weight, preferably 5 to 30% by weight, based on the total weight of component a) and the dispersant D).

Regulators

The free-radical polymerization of the monomer mixture M) can take place in the presence of at least one regulator. Regulators are preferably used in an amount of from 0.0005 to 5% by weight particularly preferably from 0.001 to 2.5% by weight and in particular from 0.01 to 1.5% by weight, based on the total weight of component a) and the dispersant D).

Regulators (polymerization regulators) is generally the term used for compounds with high transfer constants. Regulators accelerate chain-transfer reactions and thus bring about a reduction in the degree of polymerization of the resulting polymers without influencing the gross reaction rate.

With the regulators, a distinction can be made between mono-, bi- or polyfunctional regulators, depending on the number of functional groups in the molecule, which may lead to one or more chain-transfer reactions. Suitable regulators are described, for example, in detail by K. C. Berger and G. Brandrup in J. Brandrup, E. H. Immergut, Polymer Handbook, $3^{rd}$ edition, John Wiley & Sons, New. York, 1989, pp. II/81-II/141.

Suitable regulators are, for example, aldehydes, such as formaldehyde, acetaldehyde, propionaldehyde, n-butyraldehyde, isobutyraldehyde.

Further regulators which may also be used are: formic acid, its salts or esters, such as ammonium formate, 2,5-diphenyl-1-hexene, hydroxylammonium sulfate, and hydroxylammonium phosphate.

Further suitable regulators are halogen compounds, e.g. alkyl halides, such as tetrachloromethane, chloroform, bromotrichloromethane, bromoform, allylbromide, and benzyl compounds, such as benzyl chloride or benzyl bromide.

Further suitable regulators are allyl compounds, such as e.g. allyl alcohol, functionalized allyl ethers, such as allyl ethoxylates, alkyl allyl ethers, or glycerol monoallyl ether.

The regulators preferably used are compounds which contain sulfur in bonded form.

Compounds of this type are, for example, inorganic hydrogensulfites, disulfites and dithionites or organic sulfides, disulfides, polysulfides, sulfoxides and sulfones. These include di-n-butyl sulfide, di-n-octyl sulfide, diphenyl sulfide, thiodiglycol, ethylthioethanol, diisopropyl disulfide, di-n-butyl disulfide, di-n-hexyl disulfide, diacetyl disulfide, diethanol sulfide, di-t-butyl trisulfide, dimethyl sulfoxide, dialkyl sulfide, dialkyl disulfide and/or diaryl sulfide.

Particular preference is given to organic compounds which contain sulfur in bonded form.

Compounds preferably used as polymerization regulators are thiols (compounds which contain sulfur in the form of SH groups, also referred to as mercaptans). Preferred regulators are mono-, bi- and polyfunctional mercaptans, mercaptoalcohols and/or mercaptocarboxylic acids.

Examples of these compounds are allyl thioglycolates, ethyl thioglycolate, cysteine, 2-mercaptoethanol, 1,3-mercaptopropanol, 3-mercaptopropane-1,2-diol, 1,4-mercaptobutanol, mercaptoacetic acid, 3-mercaptopropionic acid, mercaptosuccinic acid, thioglycerol, thioacetic acid, thiourea, and alkyl mercaptans, such as n-butyl mercaptan, n-hexyl mercaptan or n-dodecyl mercaptan.

Particularly preferred thiols are cysteine, 2-mercaptoethanol, 1,3-mercaptopropanol, 3-mercaptopropane-1,2-diol, thioglycerol, thiourea.

Examples of bifunctional regulators which contain two sulfurs in bonded form are bifunctional thiols, such as e.g.

mercaptopropanesulfonic acid (sodium salt), dimercaptosuccinic acid, dimercapto-1-propanol, dimercaptoethane, dimercaptopropane, dimercaptobutane, dimercaptopentane, dimercaptohexane, ethylene glycolbisthioglycolates and butanediol bisthioglycolate.

Examples of polyfunctional regulators are compounds which contain more than two sulfurs in bonded form. Examples thereof are trifunctional and/or tetrafunctional mercaptans.

Preferred trifunctional regulators are trifunctional mercaptans, such as e.g. trimethylolpropane tris(2-mercaptoethanoate), trimethylolpropane tris(3-mercaptopropionate), trimethylolpropane tris(4-mercaptobutanoate), trimethylolpropane tris(5-mercaptopentanoate), trimethylolpropane tris(6-mercaptohexanoate), trimethylolpropane tris(2-mercaptoacetate), glyceryl thioglycolate, glyceryl thiopropionate, glyceryl thioethoxide, glyceryl thiobutanoate, 1,1,1-propanetriyl tris(mercaptoacetate), 1,1,1-propanetriyl tris(mercaptoethanoate), 1,1,1-propanetriyl tris(mercaptoproprionate), 1,1,1-propanetriyl tris(mercaptobutanoate), 2-hydroxmethyl-2-methyl-1,3-propanediol tris(mercaptoacetate), 2-hydroxmethyl-2-methyl-1,3-propanediol tris(mercaptoethanoate), 2-hydroxmethyl-2-methyl-1,3-propanediol tris(mercaptopropionate), 2-hydroxmethyl-2-methyl-1,3-propanediol tris(mercaptobutanoate).

Particularly preferred trifunctional regulators are glyceryl thioglycolate, trimethylolpropane tris(2-mercaptoacetate), 2-hydroxmethyl-2-methyl-1,3-propanediol tris(mercaptoacetate).

Preferred tetrafunctional mercaptans are pentaerythritol tetrakis(2-mercaptoacetate), pentaerythritol tetrakis(2-mercaptoethanoate), pentaerythritol tetrakis(3-mercaptopropionate), pentaerythritol tetrakis(4-mercaptobutanoate), pentaerythritol tetrakis(5-mercaptopentanoate), pentaerythritol tetrakis(6-mercaptohexanoate).

Further suitable polyfunctional regulators are Si compounds which arise by the reaction of compounds of the formula (IVa). Further suitable polyfunctional regulators are Si compounds of the formula (IVb).

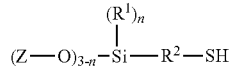

(IVa)

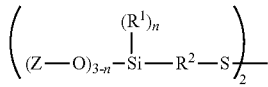

(IVb)

in which
n is a value from 0 to 2,
$R^1$ is a $C_1$-$C_{16}$-alkyl group or phenyl group,
$R^2$ is a $C_1$-$C_{18}$-alkyl group, the cyclohexyl or phenyl group,
Z is a $C_1$-$C_{16}$-alkyl group, $C_2$-$C_{18}$-alkylene group or $C_2$-$C_{18}$-alkynyl group whose carbon atoms may be replaced by nonadjacent oxygen or halogen atoms, or is one of the groups

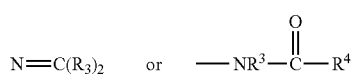

in which
$R_3$ is a $C_1$-$C_{12}$-alkyl group and
$R_4$ is a $C_1$-$C_{18}$-alkyl group.

Particular preference is given to the compounds IVa, of these primarily mercaptopropyltrimethoxysilane and mercaptopropyltriethoxysilane.

All of the regulators specified may be used individually or in combination with one another.

In a preferred embodiment of the process, multifunctional regulators are used.

For the preparation of the aqueous polymer dispersion Pd), the monomer mixture M) is polymerized in an aqueous medium in the presence of the dispersant D) in the customary manner, as are customary e.g. for processes of free-radical aqueous emulsion polymerization. The polymerization medium may here consist either only of water, or else of water and water-miscible liquids, such as alcohols, e.g. methanol, ethanol, n-propanol, isopropanol, n-butanol, tert-butanol etc. Preference is given to using only water as the polymerization medium.

The polymerization generally takes place at temperatures in a range from 0 to 150° C., preferably 20 to 100° C., particularly preferably 30 to 95° C. The polymerization preferably takes place at atmospheric pressure, but a polymerization under increased pressure, for example the autogeneous pressure of the components used for the polymerization, is also possible. If desired, the polymerization can take place in the presence of at least one inert gas, such as e.g. nitrogen.

The polymerization can be carried out either as a batch process or else in the form of a feed process, including step procedure and gradient procedure. The polymerization preferably takes place as a feed procedure in which some of the polymerization batch is initially introduced and the other components are added to the initial charge in their entirety or partially, in batches or continuously, together or in separate feeds. In this connection, preference is given to initially introducing some of the monomers used and at least some of the polymeric anionic dispersant D) and at least some of the aqueous medium into a polymerization zone, heating them to the polymerization temperature, optionally initially polymerizing this initial charge, and then introducing the remainder of the polymerization batch via one or more spatially separate feeds while maintaining the polymerization in the polymerization zone. Usually, polymerization initiator and monomers are added in separate feeds. The introduction of the monomers can take place individually or in the form of mixtures, in pure form or in dissolved form in an aqueous medium or in emulsified form.

Advantageously, the use of the polymeric anionic dispersant D) permits the preparation of aqueous polymer dispersions without the use of further interface-active substances. The dispersants D), however, may also be used in a mixture with other interface-active substances as additives.

Suitable further interface-active additives are the protective colloids and emulsifiers customarily used in emulsion polymerization as dispersants, as are described e.g. in Houben-Weyl, Methoden der organischen Chemie [Methods of Organic Chemistry], Volume XIV/1, Makromolekulare Stoffe [Macromolecular Substances], Georg-Thieme-Verlag, Stuttgart, 1961, pp. 411 to 420. Suitable additional protective colloids are e.g. polyvinyl alcohols and partially hydrolyzed vinyl acetates, polyacrylates, polyvinyl pyrrolidone, cellulose and cellulose derivatives, such as e.g. methylcellulose, hydroxyethylcellulose, carboxymethylcellulose, starch and starch derivatives, such as e.g. cyanoalkyl ether starch, hydroxyalkyl ether starch, carboxymethyl starch etc. Suitable emulsifiers are either anionic, cationic or nonionic emulsifiers.

As interface-active substances, preference is given to using emulsifiers whose relative molecular weights are, in contrast to the protective colloids, usually below 3500 daltons.

Nonionic emulsifiers which can be used are araliphatic or aliphatic nonionic emulsifiers, for example ethoxylated mono-, di- and trialkylphenols (degree of EO: 3 to 50, alkyl radical: $C_4$-$C_{10}$), ethoxylates of long-chain alcohols (degree of EO: 3 to 50, alkyl radical: $C_8$-$C_{36}$), and polyethylene oxide/polypropylene oxide block copolymers. Preference is given to ethoxylates of long-chain alkanols (alkyl radical $C_{10}$-$C_{22}$, average degree of ethoxylation 10 to 50) and of these particular preference is given to those with a linear $C_{12}$-$C_{18}$-alkyl radical and an average degree of ethoxylation of from 10 to 50, and also ethoxylated monoalkylphenols.

Suitable anionic emulsifiers are, for example, alkali metal and ammonium salts of alkyl sulfates (alkyl radical: $C_8$-$C_{22}$), of sulfuric half-esters of ethoxylated alkanols (degree of EO: 2 to 50, alkyl radical: $C_{12}$-$C_{18}$) and ethoxylated alkylphenols (degree of EO: 3 to 50, alkyl radical: $C_4$-$C_9$), of alkylsulfonic acids (alkyl radical: $C_{12}$-$C_{18}$) and of alkylarylsulfonic acids (alkyl radical: $C_9$-$C_{18}$). Further suitable emulsifiers are given in Houben-Weyl, Methoden der organischen Chemie [Methods of Organic Chemistry], Volume XIV/1, Makromolekulare Stoffe [Macromolecular substances], Georg-Thieme-Verlag, Stuttgart, 1961, pp. 192-208). Suitable anionic emulsifiers are likewise bis(phenoylsulfonic acid) ether or the alkali metal or ammonium salts thereof, which carry a $C_4$-$C_{24}$-alkyl group on one or both of the aromatic rings. These compounds are generally known, e.g. from U.S. Pat. No. 4,269,749, and are commercially available, for example as Dowfax® 2A1 (Dow Chemical Company).

Suitable cationic emulsifiers are preferably quaternary ammonium halides, e.g. trimethylcetylammonium chloride, methyltrioctylammonium chloride, benzyltriethylammonium chloride or quaternary compounds of N—$C_6$-$C_{20}$-alkylpyridines, -morpholines or -imidazoles, e.g. N-laurylpyridinium chloride.

If one of the abovementioned emulsifiers is used, then it is chosen according to the extent of its compatibility with the particular anionic polymeric dispersant D). The amount of emulsifier is generally about 0 to 10% by weight, preferably 0.01 to 5% by weight, based on the amount of monomers to be polymerized.

For the preparation of the polymer dispersions Pd) it is also possible to use polymeric dispersants which are different from the polymeric anionic dispersants D). These additional polymeric dispersants are generally used in amounts of from 0 to 10% by weight, preferably 0.01 to 5% by weight, based on the amount of monomers to be polymerized.

The additional polymeric dispersants generally contain at least one functional group chosen from ether, hydroxyl, sulfate ester, amino, imino, tert-amino, and/or quaternary ammonium groups. Examples of such compounds are: polyvinyl acetate, polyalkylene glycols, in particular polyethylene glycols, polyvinyl alcohol, polyvinylpyridine, polyethylenimine, polyvinylimidazole, polyvinylsuccinimide and polydiallyldimethylammonium chloride, polyvinylpyrrolidone, polymers which contain at least 5% by weight of a vinylpyrrolidone units, polymers which contain at least 50% by weight of vinyl alcohol units, oligosaccharides, polysaccharides, oxidatively, hydrolytically or enzymatically degraded polysaccharides, chemically modified oligo- or polysaccharides, such as, for example, carboxymethylcellulose, water-soluble starch and starch derivatives, starch esters, starch xanthanogenates, starch acetates, dextran, and mixtures thereof.

In addition, customary auxiliaries and additives may be added to the polymer dispersions. These include, for example, the pH-adjusting substances, reducing and bleaching agents, such as e.g. the alkali metal salts of hydroxymethanesulfinic acid (e.g. Rongallit® C from BASF Aktienges.), complexing agents, deodorants, odor substances and viscosity modifiers, such as alcohols, e.g. glycerol, methanol, ethanol, tert-butanol, glycol etc. These auxiliaries and additives may be added to the polymer dispersions in the initial charge, one of the feeds or after the polymerization.

The dispersions Pd) generally have a viscosity of from 100 to 50 000 mPas, preferably from 200 to 20 000 mPas, particularly preferably from 300 to 15 000 mPas.

The dispersions formed in the polymerization can, after the polymerization process, be subjected to a physical or chemical after-treatment. Such processes are, for example, the known processes of residual monomer reduction, such as e.g. after-treatment by adding polymerization initiators or mixtures of two or more polymerization initiators at suitable temperatures or heating the polymerization solution to temperatures above the polymerization temperature, an after-treatment of the polymer solution by means of water vapor or stripping with nitrogen or treatment of the reaction mixture with oxidizing or reducing reagents, adsorption processes, such as the adsorption of contamination on selected media, such as e.g. activated carbon, or an ultrafiltration. It can also be followed by the known work-up steps, for example suitable drying processes or roll-drying, or agglomeration processes following the drying. The dispersions with a low content of residual monomers obtained by the process according to the invention can also be sold directly.

The polymer dispersions Pd) can be converted into powder form by various drying processes, such as e.g. spray drying, fluidized spray drying, roll-drying or freeze-drying. Preference is given to using spray-drying. The dry polymer powders obtained in this way can advantageously be converted again into an aqueous solution or dispersion by dissolution or redispersion, respectively, in water. Pulverulent copolymers have the advantage of better storability, simpler transportability and generally have a lower tendency for microbial attack. The invention also provides the polymers P) obtainable by drying a polymer dispersion Pd).

The polymer dispersions Pd) described above and the polymers P) obtainable therefrom are highly suitable for the preparation of cosmetic and pharmaceutical compositions. They serve here e.g. as polymeric film formers in preparations for bodycare, which includes the use of cosmetic preparations on keratinous surfaces, such as skin, hair, nails, and also mouthcare preparations. They can be universally used and formulated in a very wide variety of cosmetic preparations, and are compatible with the other components. The dispersions according to the invention are characterized by a high proportion of dispersed polymer particles and a correspondingly low proportion of dissolved or swollen polymers. For the same solids content, they therefore generally exhibit significantly lower viscosities than aqueous preparations based on polymers known from the prior art. They thus permit the formulation of liquid to gel-like products with higher solids contents and are characterized by improved conditioner properties.

The invention further provides a cosmetic or pharmaceutical composition comprising
A) at least one polymer dispersion Pd), as defined above, or a polymer P), as defined above, and
B) at least one cosmetically acceptable carrier.

The compositions according to the invention have a cosmetically or pharmaceutically acceptable carrier B) which is chosen from i) water,
ii) water-miscible organic solvents, preferably $C_1$-$C_4$-alkanols,
iii) oils, fats, waxes,
iv) esters of $C_6$-$C_{30}$-monocarboxylic acids with mono-, di- or trihydric alcohols which are different from iii),
v) saturated acyclic and cyclic hydrocarbons,
vi) fatty acids,
vii) fatty alcohols and mixtures thereof.

The compositions according to the invention have, for example, an oil or fat component B) which is chosen from: hydrocarbons of low polarity, such as mineral oils; linear saturated hydrocarbons, preferably with more than 8 carbon atoms, such as tetradecane, hexadecane, octadecane etc.; cyclic hydrocarbons, such as decahydronaphthalene; branched hydrocarbons; animal and vegetable oils; waxes; wax esters; petroleum jelly; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1 000 to 150 000 g/mol. Preferred cyclic siloxanes have 4- to 8-membered rings. Suitable cyclic siloxanes are commercially available, for example, under the name cyclomethicone.

Preferred oil or fat components B) are chosen from paraffin and paraffin oils; petroleum jelly; natural fats and oils, such as castor oil, soybean oil, groundnut oil, olive oil, sunflower oil, sesame oil, avocado oil, cocoa butter, almond oil, peach kernel oil, castor oil, cod-liver oil, lard, spermaceti, spermaceti oil, sperm oil, wheatgerm oil, *macadamia* nut oil, evening primrose oil, jojoba oil; fatty alcohols, such as lauryl alcohol, myristyl alcohol, cetyl alcohol, stearyl alcohol, oleyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti and mixtures of the abovementioned oil and fat components.

Suitable cosmetically and pharmaceutically compatible oil or fat components B) are described in Karl-Heinz Schrader, Grundlagen und Rezepturen der Kosmetika [Fundamentals and formulations of cosmetics], 2nd edition, Verlag Hüthig, Heidelberg, pp. 319-355, which is hereby incorporated by reference.

Suitable hydrophilic carriers B) are chosen from water, 1-, 2- or polyhydric alcohols with preferably 1 to 8 carbon atoms, such as ethanol, n-propanol, isopropanol, propylene glycol, glycerol, sorbitol, etc.

The cosmetic compositions according to the invention may be skin cosmetic, hair cosmetic, dermatological, hygienic or pharmaceutical compositions. On the basis of their film-forming properties, the above-described polymers P) and polymer dispersions Pd) are suitable in particular as additives for hair and skin cosmetics.

The compositions according to the invention are preferably in the form of a gel, foam, spray, ointment, cream, emulsion, suspension, lotion, milk or paste. If desired, liposomes or microspheres can also be used.

The cosmetically or pharmaceutically active compositions according to the invention can additionally comprise cosmetically and/or dermatologically active ingredients and auxiliaries.

The cosmetic compositions according to the invention preferably comprise at least one polymer P) as defined above or a polymer dispersion Pd), at least one carrier B) as defined above and at least one constituent different from P) or Pd) which is chosen from cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tinting agents, tanning agents, dyes, pigments, consistency-imparting agents, humectants, refatting agents, collagen, protein hydrolyzates, lipids, antioxidants, antifoams, antistats, emollients and softeners.

Customary thickeners in such formulations are crosslinked polyacrylic acids and derivatives thereof, polysaccharides, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Suitable thickeners are also the Aculyn® grades from Rohm und Haas, such as Aculyn® 22 (copolymer of acrylates and methacrylic acid ethoxylates with stearyl radical (20 EO units)) and Aculyn® 28 (copolymer of acrylates and methacrylic acid ethoxylates with behenyl radical (25 EO units)).

Suitable cosmetically and/or dermatologially active ingredients are, for example, coloring active ingredients, skin and hair pigmentation agents, tinting agents, tanning agents, bleaches, keratin-hardening substances, antimicrobial active ingredients, light filter active ingredients, repellent active ingredients, substances with a hyperemic effect, substances with a keratolytic and keratoplastic effect, antidandruff active ingredients, antiphlogistics, substances with a keratinizing effect, active ingredients with an antioxidative effect or a free-radical scavenging effect, substances which wet the skin or retain moisture, refatting active ingredients, antierythematous or antiallergic active ingredients and mixtures thereof.

Active ingredients which tan the skin artifically and which are suitable for tanning the skin without natural or artificial irradiation with UV rays are, for example, dihydroxyacetone, alloxan and walnut shell extract. Suitable keratin-hardening substances are usually active ingredients as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus serve both as preservatives and also as a deodorizing substance which reduces the formation or the intensity of body odor. These include, for example, customary preservatives known to the person skilled in the art, such as p-hydroxybenzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable light filter active ingredients are substances which absorb UV rays in the UV-B- and/or UV-A region. Suitable UV filters are, for example, 2,4,6-triaryl-1,3,5-triazines in which the aryl groups may in each case carry at least one substituent which is preferably chosen from hydroxy, alkoxy, specifically methoxy, alkoxycarbonyl, specifically methoxycarbonyl and ethoxycarbonyl and mixtures thereof. Also suitable are p-aminobenzoates, cinnamates, benzophenones, camphor derivatives, and pigments which stop UV rays, such as titanium dioxide, talc and zinc oxide. Suitable repellent active ingredients are compounds which are able to drive away or keep certain animals, in particular insects, away from humans. These include, for example, 2-ethyl-1,3-hexanediol, N,N-diethyl-m-toluamide etc. Suitable substances with hyperemic activity, which stimulate blood flow through the skin are, for example, essential oils, such as dwarf pine, lavender, rosemary, juniperberry, roast chestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counter skin irritations, are, for example, allantoin, bisabolol, Dragosantol, camomile extract, panthenol, etc.

The cosmetic compositions according to the invention can comprise, as cosmetic and/or pharmaceutical active ingredient (and also optionally as auxiliary), at least one cosmetically or pharmaceutically acceptable polymer different from P) or Pd). Very generally, these include anionic, cationic, amphoteric and neutral polymers.

Examples of anionic polymers are homopolymers and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luviflex® Soft and Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxyfunctional ones, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are available commercially under the names Resyn® (National Starch) and Gafset® (GAF), and vinylpyrrolidone/vinyl acrylate copolymers obtainable, for example, under the trade name Luviflex® (BASF). Further suitable polymers are the vinylpyrrolidone/acrylate terpolymer obtainable under the name Luviflex® VBM-35 (BASF), and sodium sulfonate-containing polyamides or sodium sulfonate-containing polyesters.

The group of polymers suitable for combination with the polymers according to the invention further includes, for example, Balance® CR (National Starch; acrylate copolymer), Balance® 0/55 (National Starch; acrylate copolymer), Balance® 47 (National Starch; octylacrylamide/acrylates/butylaminoethyl methacrylates copolymer), Aquaflex® FX 64 (ISP; isobutylene/ethylmaleimide/hydroxyethylmaleimide copolymer), Aquaflex® SF-40 (ISP/National Starch; VP/vinyl caprolactam/DMAPA acrylate copolymer), Allianz® LT-120 (ISP/Rohm & Haas; acrylate/C1-2 succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxides/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylate copolymer), Aculyne® 258 (Rohm & Haas; acrylate/hydroxy ester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), DynamX (National Starch; polyurethane-14 AMP-acrylates copolymer), Resyn XP (National Starch; acrylates/octylacrylamide copolymer), Fixomer A-30 (Ondeo Nalco; polymethacrylic acid (and) acrylamidomethylpropanesulfonic acid), Fixate G-100 (Noveon; AMP-acrylates/allyl methacrylate copolymer).

Further suitable polymers are cationic polymers with the INCI name Polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), Polymer JR (hydroxyethylcellulose with cationic groups) and plant-based cationic polymers, e.g. guar polymers, such as the Jaguar® grades from Rhodia.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethylenimines and salts thereof, polyvinylamines and salts thereof, cellulose derivatives, polyaspartic acid salts and derivatives. These include, for example, Luviflex® Swing (partially hydrolyzed copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF) or polyvinylpyrrolidone and copolymers thereof, in particular with vinyl esters, such as vinyl acetate, e.g. Luviskol® VA 37 (BASF); polyamides, e.g. based on itaconic acid and aliphatic diamines, as are described, for example, in DE-A-43 33 238.

Suitable polymers are also amphoteric or zwitterionic polymers, such as the octyl acrylamide/methyl methacrylate/tert-butylaminoethyl methacrylate/2-hydroxypropyl methacrylate copolymers and zwitterionic polymers as are disclosed, for example, in German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers which are available commercially under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyethersiloxanes, such as Tegopren® (Goldschmidt) or Belsil® (Wacker).

The formulation base of pharmaceutical compositions according to the invention preferably comprises pharmaceutically acceptable auxiliaries. Pharmaceutically acceptable auxiliaries are the auxiliaries which are known for use in the field of pharmacy, food technology and related fields, in particular those listed in the relevant pharmacopoeia (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, antiirritative substances, chelating agents, emulsion stabilizers, film formers, gel formers, odor-masking agents, resins, hydrocolloids, solvents, solubility promoters, neutralizing agents, permeation accelerators, pigments, quaternary ammonium compounds, refatting and superfatting agents, ointment bases, cream bases or oil bases, silicone derivatives, stabilizers, sterilizing agents, propellants, drying agents, opacifiers, thickeners, waxes, softeners, white oils. Formulation in this regard is based on specialist knowledge, as given, for example, in Fiedler, H. P. Lexikon der Hilfstoffe für Pharmazie, Kosmetik und angrenzende Gebiete [Lexicon of auxiliaries for pharmacy, cosmetics and related fields], 4th ed., Aulendorf: ECV-Editio-Kantor-Verlag, 1996.

To prepare the dermatological compositions according to the invention, the active ingredients can be mixed or diluted with a suitable auxiliary (excipient). Excipients may be solid, semisolid or liquid materials which can also serve as vehicles, carriers or medium for the active ingredient. The admixing of further auxiliaries is carried out, where desired, in the manner known to the person skilled in the art. In addition, the polymers P) and dispersions Pd) are suitable as auxiliaries in pharmacy, preferably as a or in coating(s) or binder(s) for solid drug forms. They can also be used in creams and as tablet coatings and tablet binders.

According to a preferred embodiment, the compositions according to the invention are a skin-cleansing composition.

Preferred skin-cleansing compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations, shaving foams, lotions and creams.

According to a further preferred embodiment, the compositions according to the invention are cosmetic compositions for the care and protection of the skin, nailcare compositions or preparations for decorative cosmetics.

Suitable skin cosmetic compositions are, for example, face tonics, face masks, deodorants and other cosmetic lotions. Compositions for use in decorative cosmetics include, for example, concealer pencils, stage makeup, mascara and eyeshadows, lipsticks, kohl pencils, eyeliners, blushers, powders and eyebrow pencils.

Furthermore, the polymers P) and dispersions Pd) can be used in nose strips for pore cleansing, in antiacne compositions, repellents, shaving compositions, hair-removal compositions, personal hygiene compositions, footcare compositions, and in babycare.

The skincare compositions according to the invention are, in particular, W/O or O/W skin creams, day and night creams, eye creams, face creams, antiwrinkle creams, moisturizing creams, bleaching creams, vitamin creams, skin lotions, care lotions and moisturizing lotions.

Skin cosmetic and dermatological compositions based on the above-described polymers P) and dispersions Pd) exhibit advantageous effects. The polymers can, inter alia, contribute to the moisturization and conditioning of the skin and to an improvement in the feel of the skin. The polymers can also act as thickeners in the formulations. By adding the polymers according to the invention, it is possible to achieve a considerable improvement in skin compatibility in certain formulations.

Skin cosmetic and dermatological compositions preferably comprise at least one polymer P), optionally in the form of a dispersion Pd) in an amount of from about 0.001 to 30% by weight, preferably 0.01 to 20% by weight, very particularly preferably 0.1 to 12% by weight, based on the total weight of the composition.

Light protection agents based on the polymers P) and dispersions Pd), in particular, have the property of increasing the residence time of the UV-absorbing ingredients compared with customary auxiliaries such as polyvinylpyrrolidone.

Depending on the field of use, the compositions according to the invention can be applied in a form suitable for skincare, such as, for example, in the form of a cream, foam, gel, pencil, mousse, milk, spray (pump spray or spray containing propellant) or lotion.

As well as comprising the polymers P) and dispersions Pd) and suitable carriers, the skin cosmetic preparations can also comprise further active ingredients and auxiliaries customary in skin cosmetics and as described above. These include, preferably, emulsifiers, preservatives, perfume oils, cosmetic active ingredients, such as phytantriol, vitamin A, E and C, retinol, bisabolol, panthenol, light protection agents, bleaches, colorants, tinting agents, tanning agents, collagen, protein hydrolyzates, stabilizers, pH regulators, dyes, salts, thickeners, gel formers, consistency-imparting agents, silicones, humectants, refatting agents and further customary additives.

Preferred oil and fat components of the skin cosmetic and dermatological compositions are the abovementioned mineral and synthetic oils, such as, for example, paraffins, silicone oils and aliphatic hydrocarbons with more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, petroleum jelly, hydrogenated lanolin and acetylated lanolin, and mixtures thereof.

The polymers according to the invention can also be mixed with conventional polymers where specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are prepared by customary processes known to the person skilled in the art.

The cosmetic and dermatological compositions are preferably in the form of emulsions, in particular in the form of water-in-oil (W/O) or oil-in-water (O/W) emulsions. It is, however, also possible to choose other types of formulation, for example hydrodispersions, gels, oils, oleogels, multiple emulsions, for example in the form of W/O/W or O/W/O emulsions, anhydrous ointments or ointment bases, etc.

The emulsions are prepared by known methods. Apart from at least one polymer P), the emulsions usually comprise customary constituents, such as fatty alcohols, fatty acid esters and in particular fatty acid triglycerides, fatty acids, lanolin and derivatives thereof, natural or synthetic oils or waxes and emulsifiers in the presence of water. The choice of emulsion type-specific additives and the preparation of suitable emulsions is described, for example, in Schrader, Grundlagen und Rezepturen der Kosmetika [Fundamentals and formulations of cosmetics], Hüthig Buch Verlag, Heidelberg, 2nd edition, 1989, third part, which is hereby expressly incorporated by reference.

A suitable emulsion, e.g. for a skin cream etc., generally comprises an aqueous phase which is emulsified by means of a suitable emulsifier system in an oil or fatty phase. A polymer dispersion Pd) can be used to prepare the aqueous phase.

The proportion of the emulsifier system in this type of emulsion is preferably about 4 to 35% by weight, based on the total weight of the emulsion. The proportion of the fatty phase is preferably about 20 to 60% by weight. The proportion of the aqueous phase is preferably about 20 to 70% by weight, in each case based on the total weight of the emulsion. The emulsifiers are those customarily used in this type of emulsion. They are chosen, for example, from: $C_{12}$-$C_{18}$-sorbitan fatty acid esters; esters of hydroxystearic acid and $C_{12}$-$C_{30}$-fatty alcohols; mono- and diesters of $C_{12}$-$C_{18}$-fatty acids and glycerol or polyglycerol; condensates of ethylene oxide and propylene glycols; oxypropylenated/oxyethylated $C_{12}$-$C_{18}$-fatty alcohols; polycyclic alcohols, such as sterols; aliphatic alcohols with a high molecular weight, such as lanolin; mixtures of oxypropylenated/polyglycerolated alcohols and magnesium isostearate; succinic esters of polyoxyethylenated or polyoxypropylenated fatty alcohols; and mixtures of magnesium lanolate, calcium lanolate, lithium lanolate, zinc lanolate or aluminum lanolate and hydrogenated lanolin or lanolin alcohol.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karité oil, hoplostethus oil; mineral oils whose distillation start-point under atmospheric pressure is about 250° C. and whose distillation end-point is 410° C., such as, for example, vaseline oil; esters of saturated or unsaturated fatty acids, such as alkyl myristates, e.g. i-propyl, butyl or cetyl myristate, hexadecyl stearate, ethyl or isopropyl palmitate, octanoic or decanoic acid triglycerides and cetyl ricinoleate.

The fatty phase can also comprise silicone oils soluble in other oils, such as dimethylpolysiloxane, methylphenylpolysiloxane and the silicone glycol copolymer, fatty acids and fatty alcohols.

In order to favor the retention of oils, as well as the polymers P), it is also possible to use waxes, such as, for example, carnauba wax, candililla wax, beeswax, microcrystalline wax, ozokerite wax and the oleates, myristates, linoleates and stearates of Ca, Mg and Al.

The water-in-oil emulsions are generally prepared by introducing the fatty phase and the emulsifier into a reaction vessel. The vessel is heated at a temperature of approximately 50 to 75° C., then the oil-soluble active ingredients and/or auxiliaries are added, and water which has been heated beforehand to approximately the same temperature and into which the water-soluble ingredients have optionally been dissolved beforehand is added with stirring. The mixture is stirred until an emulsion of the desired fineness is achieved, which is then left to cool to room temperature, if necessary with a lesser amount of stirring.

In addition, a care emulsion according to the invention may be in the form of an O/W emulsion. Such an emulsion usually comprises an oil phase, emulsifiers which stabilize the oil phase in the water phase, and an aqueous phase which is usually present in thickened form.

The aqueous phase of the O/W emulsion of the preparations according to the invention optionally comprises:
  alcohols, diols or polyols, and ethers thereof, preferably ethanol, isopropanol, propylene glycol, glycerol, ethylene glycol monoethyl ether;
  customary thickeners or gel formers, such as, for example, crosslinked polyacrylic acids and derivatives thereof, polysaccharides, such as xanthan gum or alginates, carboxymethylcellulose or hydroxycarboxymethylcellulose, fatty alcohols, polyvinyl alcohol and polyvinylpyrrolidone.

The oil phase comprises oil components customary in cosmetics, such as, for example:
  esters of saturated and/or unsaturated, branched and/or unbranched $C_3$-$C_{30}$-alkanecarboxylic acids and saturated and/or unsaturated, branched and/or unbranched $C_3$-$C_{30}$-alcohols, of aromatic carboxylic acids and saturated and/or unsaturated, branched and/or unbranched $C_3$-$C_{30}$-alcohols, for example isopropyl myristate, isopropyl stearate, hexyldecyl stearate, oleyl oleate; and also synthetic, semisynthetic and natural mixtures of such esters, such as jojoba oil;
  branched and/or unbranched hydrocarbons and hydrocarbon waxes;
  silicone oils, such as cyclomethicone, dimethylpolysiloxane, diethylpolysiloxane, octamethylcyclotetrasiloxane and mixtures thereof;
  dialkyl ethers;
  mineral oils and mineral waxes;
  triglycerides of saturated and/or unsaturated, branched and/or unbranched $C_8$-$C_{24}$-alkanecarboxylic acids; they can be chosen from synthetic, semisynthetic or natural oils, such as olive oil, palm oil, almond oil or mixtures.

Suitable emulsifiers are preferably O/W emulsifiers, such as polyglycerol esters, sorbitan esters or partially esterified glycerides.

The preparation can take place by melting the oil phase at about 80° C.; the water-soluble constituents are dissolved in hot water, and added to the oil phase slowly and with stirring; the mixture is homogenized and stirred until cold.

According to a further preferred embodiment, the compositions according to the invention are a shower gel, a shampoo formulation or a bath preparation.

Such formulations comprise at least one polymer P) or a dispersion Pd) and customary anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickeners/gel formers, skin conditioning agents and humectants.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants customarily used in body-cleansing compositions can be used in washing, shower and bath preparations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or alkyl amphopropionates, alkyl amphodiacetates or alkyl amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The washing, shower and bath preparations can also comprise customary cationic surfactants, such as, for example, quaternary ammonium compounds, for example cetyltrimethylammonium chloride.

In addition, it is also possible to use other customary cationic polymers, such as, for example, copolymers of acrylamide and dimethyldiallylammonium chloride (Polyquaternium-7), cationic cellulose derivatives (Polyquaternium-4, -10), guar hydroxypropyltrimethylammonium chloride (INCI: Hydroxylpropyl Guar Hydroxypropyltrimonium Chloride), copolymers of N-vinylpyrrolidone and quaternized N-vinylimidazole (Polyquaternium-16, -44, -46), copolymers of N-vinylpyrrolidone/dimethylaminoethyl methacrylate, quaternized with diethyl sulfate (Polyquaternium-11) and others.

In addition, the shower gel/shampoo formulations may comprise thickeners, such as, for example, sodium chloride, PEG-55, propylene glycol oleate, PEG-120-methylglucose dioleate and others, and also preservatives, further active ingredients and auxiliaries and water.

According to a further preferred embodiment, the compositions according to the invention are a hair-treatment composition.

Hair-treatment compositions according to the invention preferably comprise at least one polymer P) in an amount in the range from about 0.1 to 30% by weight, preferably 0.5 to 20% by weight, based on the total weight of the composition.

The hair-treatment compositions according to the invention are preferably in the form of a setting foam, hair mousse, hair gel, shampoo, hairspray, hair foam, end fluid, neutralizing agent for permanent waves, hair colorant and bleach or hot-oil treatment.

Depending on the field of use, the hair cosmetic preparations can be applied in the form of an (aerosol) spray, (aerosol) foam, gel, gel spray, cream, lotion or wax. Hairsprays include both aerosol sprays and also pump sprays without propellant gas. Hair foams include both aerosol foams and also pump foams without propellant gas. Hairsprays and hair foams preferably comprise predominantly or exclusively water-soluble or water-dispersible components. If the compounds used in the hairsprays and hair foams according to the invention are water-dispersible, they can be applied in the form of aqueous microdispersions with particle diameters of usually 1 to 350 nm, preferably 1 to 250 nm. The solids contents of these preparations here are usually in a range from about 0.5 to 20% by weight. These microdispersions generally require no emulsifiers or surfactants for their stabilization.

In a preferred embodiment, the hair cosmetic formulations according to the invention comprise
a) 0.05 to 20% by weight of at least one polymer P),
b) 20 to 99.95% by weight of water and/or alcohol,
c) 0 to 79.5% by weight of further constituents.

Alcohol is understood as meaning all alcohols customary in cosmetics, e.g. ethanol, isopropanol, n-propanol.

Further constituents are understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances, such as panthenol, collagen, vitamins, protein hydrolyzates, alpha- and beta-hydroxycarboxylic acids, stabilizers, pH regulators, dyes, viscosity regulators, gel formers, salts, humectants, refatting agents, complexing agents and further customary additives.

These also include all styling and conditioning polymers known in cosmetics which may be used in combination with the polymers according to the invention if very particular properties are to be set.

Suitable conventional hair cosmetic polymers are, for example, the abovementioned cationic, anionic, neutral, nonionic and amphoteric polymers, which are hereby incorporated by reference.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and aminofunctional silicone compounds such as amodimethicone (CTFA).

The polymers according to the invention are suitable in particular as setting agents in hairstyling preparations, in particular hairsprays (aerosol sprays and pump sprays without propellant gas) and hair foams (aerosol foams and pump foams without propellant gas).

In a preferred embodiment, these preparations comprise
a) 0.1 to 10% by weight of at least one polymer P),
b) 20 to 99.9% by weight of water and/or alcohol,
c) 0 to 70% by weight of at least one propellant,
d) 0 to 20% by weight of further constituents.

Propellants are the propellants customarily used for hairsprays or aerosol foams. Preference is given to mixtures of propane/butane, pentane, dimethyl ether, 1,1-difluoroethane (HFC-152 a), carbon dioxide, nitrogen or compressed air.

A formulation for aerosol hair foams preferred according to the invention comprises
a) 0.1 to 10% by weight of at least one polymer P),
b) 55 to 99.8% by weight of water and/or alcohol,
c) 5 to 20% by weight of a propellant,
d) 0.1 to 5% by weight of an emulsifier,
e) 0 to 10% by weight of further constituents.

Emulsifiers which may be used are all emulsifiers customarily used in hair foams. Suitable emulsifiers may be nonionic, cationic or anionic or amphoteric.

Examples of nonionic emulsifiers (INCI nomenclature) are Laureths, e.g. Laureth-4; Ceteths, e.g. Ceteth-1, polyethylene glycol cetyl ether; Cetearaths, e.g. Ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methylsulfate, Quaternium-1 to x (INCI).

Anionic emulsifiers can, for example, be chosen from the group of alkylsulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the following composition:
a) 0.1 to 10% by weight of at least one polymer P),
b) 60 to 99.85% by weight of water and/or alcohol,
c) 0.05 to 10% by weight of a gel former,
d) 0 to 20% by weight of further constituents.

Gel formers which can be used are all gel formers customary in cosmetics. These include slightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylates copolymer, Polyquaternium-32 (and) Paraffinum Liquidum (INCI), sodium acrylates copolymer (and) Paraffinum Liquidum (and) PPG-1 Trideceth-6, Acrylamidopropyl Trimonium Chloride/Acrylamide Copolymer, Steareth-10 Allyl Ether Acrylates Copolymer, Polyquaternium-37 (and) Paraffinum Liquidum (and) PPG-1 Trideceth-6, Polyquaternium 37 (and) Propylene Glycol Dicaprate Dicaprylate (and) PPG-1 Trideceth-6, Polyquaternium-7, Polyquaternium-44.

The polymers P) and dispersions Pd) according to the invention can be used in cosmetic preparations as conditioning agents.

The polymers P) and dispersions Pd) according to the invention can preferably be used in shampoo formulations as setting and/or conditioning agents. Preferred shampoo formulations comprise
a) 0.05 to 10% by weight of at least one polymer P),
b) 25 to 94.95% by weight of water,
c) 5 to 50% by weight of surfactants,
c) 0 to 5% by weight of a further conditioning agent,
d) 0 to 10% by weight of further cosmetic constituents.

All anionic, neutral, amphoteric or cationic surfactants customarily used in shampoos can be used in the shampoo formulations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

For example, sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate are suitable.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, alkylpolyglycosides or sorbitan ether esters.

Furthermore, the shampoo formulations can comprise customary cationic surfactants, such as, for example, quaternary ammonium compounds, for example cetyltrimethylammonium chloride.

In the shampoo formulations, customary conditioning agents can be used in combination with the polymers P) to achieve certain effects. These include, for example, the abovementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamide copolymers (Polyquaternium-7). It is also possible to use protein hydrolyzates, and conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and aminofunctional silicone compounds, such as amodimethicone (CTFA). In addition, cationic guar derivatives, such as guar hydroxypropyltrimonium chloride (INCI) can be used.

The invention is illustrated in more detail by reference to the following nonlimiting examples.

EXAMPLES

Example 1

312 g of sodium salt (40% strength aqueous solution) of a maleic acid-acrylic acid copolymer (Sokalan® CP 5 from BASF AG, 7 parts of acrylic acid and 3 parts of maleic acid, Mn=70 000), 160 g of vinylpyrrolidone, 88.9 g of N-vinyl-2-methylimidazolium methylsulfate (45% strength aqueous solution) and 0.3 g of triallylamine were initially introduced into 146.2 g of water in a stirred apparatus fitted with anchor stirrer (200 rpm), nitrogen inlet and separate feed device, and the pH of the solution was adjusted to 6.8 by adding 7.5 g of sulfuric acid (50% strength aqueous solution). Nitrogen was passed continuously through the reaction mixture and the reaction mixture was heated to a temperature of 65° C. for the polymerization. Within three hours, 100 g of a 1.5% strength by weight solution of 2,2'-azobis-2-(aminopropane) dihydrochloride (WAKO® V 50) were run in. When the run-in period was over, the mixture was polymerized for a further four hours. The polymerization temperature was then increased to 70° C., and a further 100 g of a 1.5% strength by weight solution of 2,2'-azobis-2-(aminopropane) dihydrochloride (WAKO® V 50) were added over the course of one hour. The mixture was then polymerized once again for two hours at 70° C. The resulting dispersion had an active ingredient content of 20% and a solids content of 32.5%. The LT value of the dispersion was <0.05 and the viscosity was 8 000 mPas.

Example 2

312 g of sodium salt (40% strength aqueous solution) of a maleic acid-acrylic acid copolymer (Sokalan® CP 5 from BASF AG, 7 parts of acrylic acid and 3 parts of maleic acid, Mn=70 000), 42 g of vinylpyrrolidone, 31.10 g of N-vinyl-2-methylimidazolium methylsulfate (45% strength aqueous solution) and 0.7 g of triallylamine were initially introduced into 146.2 g of water in a stirred apparatus with anchor stirrer (200 rpm), nitrogen inlet and separate feed device, and the pH of the solution was adjusted to 6.8 by adding 7 g of sulfuric acid (50% strength aqueous solution). Nitrogen was passed continuously through the reaction mixture, and the reaction mixture was heated to a temperature of 65° C. for the polymerization. Over the course of two hours, 168 g of vinylpyrrolidone, 124.4 g of vinylimidazolium dimethylsulfate and 116.8 g of water were run in, and over the course of three hours, 100 g of a 1.5% strength by weight solution of 2,2'-azobis-2-(aminopropane) dihydrochloride (WAKO® V 50) were run in. The polymerization time following these introductions was four hours. The polymerization temperature was then increased to 70° C. and a further 100 g of a 1.5% strength by weight solution of 2,2'-azobis-2-(aminopropane) dihydrochloride (WAKO® V 50) were added over the course of one hour. The mixture was then polymerized for a further two hours at 70° C. The dispersion has an active ingredient content of 20% and a solids content of 32.5%. The LT value of the dispersion was <0.05 and the viscosity was 8 500 mPas.

Example 3

312 g of sodium salt (40% strength aqueous solution) of a maleic acid-acrylic acid copolymer (Sokalan® CP 7 from BASF AG), 33 g of vinylpyrrolidone, 24.90 g of N-vinyl-2-methylimidazolium methylsulfate (45% strength aqueous solution) and 0.7 g of triallylamine were initially introduced into 146.2 g of water in a stirred apparatus fitted with anchor stirrer (200 rpm), nitrogen inlet and separate feed device, and the pH of the solution was adjusted to 6.8 by adding 7 g of sulfuric acid (50% strength aqueous solution). Nitrogen was passed continuously through the reaction mixture the reaction mixture was heated to a temperature of 65° C. for the polymerization. Over the course of 2.5 hours, 134 g of vinylpyrrolidone, 44.8 g of methyl acrylate, 99.1 g of vinylimidazolium dimethylsulfate and 130.9 g of water were run in, and over the course of three hours, 100 g of a 1.5% strength by weight solution of 2,2'-azobis-2-(aminopropane) dihydrochloride (WAKO® V 50) were run in. The polymerization time following these introductions was four hours. The polymerization temperature was then increased to 70° C. and a further 100 g of a 1.5% strength by weight solution of 2,2'-azobis-2-(aminopropane) dihydrochloride (WAKO® V 50) were added over the course of one hour. The mixture was then polymerized for a further two hours at 80° C. The dispersion has an active ingredient content of 20% and a solids content of 32.5%. The LT value of the dispersion was <0.05 and the viscosity was 12 100 mPas.

This gave an aqueous dispersion with a solids content of 20%, a viscosity of 8 000 mPas and an LT value (measured at an active ingredient content of 20%) of <1% (0.01).

The polymer dispersions of comparative examples 1 and 2 were obtained analogously to Example 1. Their composition is given in Table 1.

The Brookfield viscosity measurement was measured at 25° C., using spindle 4 and 12 revolutions.

The combing force decrease was determined as follows:

Determination of the blank value for wet combability: the washed hair was dried overnight in a climatically controlled room. Prior to measurement, it was shampooed twice with Texapon NSO for a total of one minute and rinsed for one minute so that it is definitely wet, i.e. swollen. Prior to the start of the measurement, the tress was precombed until knots are no longer present in the hair and thus a constant application of force is required during repeated measurement combing. The tress was then fixed to the support and combed using the finely-toothed side of the comb into the finely-toothed side of the test comb. The hair was inserted into the test comb for each measurement uniformly and without tension. The measurement was started and evaluated by means of software (EGRANUDO Program, Frank). The individual measurement was repeated 5 to 10 times. The calculated average value was noted.

Determination of the measurement value for wet combability: following the determination of the blank value, the hair was treated with a shampoo comprising the dispersion according to the invention or one comprising the comparison dispersion according to Table 1. The combing force is measured analogously to the blank-value determination.

Evaluation:

Reduction in combing force wet [%]=100−(measurement value*100/blank value)

The grade awarded was ascertained in accordance with the following scale: 1 very good, 2 satisfactory, 3 unsatisfactory

TABLE 1

| Example No. | VP[1] [% by wt.] | QVI[2] [% by wt.] | TAA[3] [% by wt.] | CP5[4] [% by wt.] | Reduction in combing force % | Grade |
|---|---|---|---|---|---|---|
| 1 | 80 | 20 | 0.15 | 12.5 | 60 | 1- |
| C1 | 80 | 20 | 0.15 | 0 | 26 | 2- |
| C2 | 80 | 20 | 0 | 12.5 | 23 | 2-3 |

[1]Vinylpyrrolidone
[2]N-Vinyl-2-methylimidazolium methylsulfate
[3]Triallylamine
[4]Copolymer of 7 parts of acrylic acid and 3 parts of maleic acid, sodium salt (Sokalan ® CP 5
[5]based on VP and QVI The dispersion according to the invention (Example 1) displays excellent hair cosmetic properties. It can be prepared with a comparatively high solids content at the desired viscosity. The corresponding dispersions, prepared without crosslinker (Comparative example C2) display unsatisfactory hair cosmetic properties. The preparation in the presence of a crosslinker is absolutely necessary to achieve the performance properties. Polymers which are prepared without polymeric dispersants (Comparative example C1). In addition, their hair cosmetic properties are unsatisfactory compared to those of the dispersion according to the invention. For the preparation of polymers which are regarded as being excellent in terms of performance, therefore, the presence of a suitable polymeric dispersant is required.

Examples of Cosmetic Preparations (All Data in % by Weight)

The dispersion obtained in Example 1 was used in all of the formulations.

Example 1

Liquid Makeup

| | A |
|---|---|
| 1.70 | Glyceryl stearate |
| 1.70 | Cetyl alcohol |
| 1.70 | Ceteareth-6 |
| 1.70 | Ceteareth-25 |
| 5.20 | Caprylic/Capric Triglyceride |
| 5.20 | Mineral oil |
| | B |
| q.s. | Preservative |
| 4.30 | Propylene glycol |
| 2.50 | Dispersion according to the invention |
| 59.50 | Dist. water |
| | C |
| q.s. | Perfume oil |
| | D |
| 2.00 | Iron oxide |
| 12.00 | Titanium dioxide |

Preparation:

Heat Phase A and Phase B separately from one another to 80° C. Then mix Phase B into Phase A with a stirrer. Allow everything to cool to 40° C. and add Phase C and Phase D. Homogenize repeatedly.

Example 2

Oil-free Makeup

| | A |
|---|---|
| 0.35 | Veegum |
| 5.00 | Butylene glycol |
| 0.15 | Xanthan gum |
| | B |
| 53.00 | Dist. water |
| q.s. | Preservative |
| 0.20 | Polysorbate-20 |
| 1.60 | Tetrahydroxypropylethylenediamine |

-continued

| | C |
|---|---|
| 1.00 | Silicon dioxide |
| 2.00 | Nylon-12 |
| 4.15 | Mica |
| 6.00 | Titanium dioxide |
| 1.85 | Iron oxides |
| | D |
| 4.00 | Stearic acid |
| 1.50 | Glyceryl stearate |
| 7.00 | Benzyl laurate |
| 5.00 | Isoeicosane |
| q.s. | Preservative |
| | E |
| 1.00 | Dist. water |
| 0.50 | Panthenol |
| 0.10 | Imidazolidinylurea |
| 5.00 | Dispersion according to the invention |

Preparation:

Wet Phase A with butylene glycol, add to Phase B and mix thoroughly. Heat Phase AB to 75° C. Pulverize Phase C feed substances, add to Phase AB and homogenize thoroughly. Mix feed substances of Phase D, heat to 80° C. and add to Phase ABC. Mix for some time until everything is homogeneous. Transfer everything to a vessel with propeller mixer. Mix feed substances of Phase E, add to Phase ABCD and mix thoroughly.

Example 3

Eyeliner

| | A |
|---|---|
| 40.60 | Dist. water |
| 0.20 | Disodium EDTA |
| q.s. | Preservative |
| | B |
| 0.60 | Xanthan gum |
| 0.40 | Veegum |
| 3.00 | Butylene glycol |
| 0.20 | Polysorbate-20 |
| | C |
| 15.00 | Iron oxide/Al Powder/Silicone dioxide (e.g. Sicopearl Fantastico Gold ™ from BASF) |
| | D |
| 10.00 | Dist. water |
| 30.00 | Dispersion according to the invention |

Preparation:

Premix Phase B. Using a propeller mixer, mix Phase B into Phase A, allowing the thickener to swell. Wet Phase C with Phase D. Add everything to Phase AB and mix thoroughly.

Example 4

Simmering Gel

| | A |
|---|---|
| 32.60 | Dist. water |
| 0.10 | Disodium EDTA |
| 25.00 | Carbomer (2% strength aqueous solution) |
| 0.30 | Preservative |

-continued

B

| | |
|---|---|
| 0.50 | Dist. water |
| 0.50 | Triethanolamine |

C

| | |
|---|---|
| 10.00 | Dist. water |
| 9.00 | Dispersion according to the invention |
| 1.00 | Polyquaternium-46 |
| 5.00 | Iron oxide |

D

| | |
|---|---|
| 15.00 | Dist. water |
| 1.00 | D-Panthenol 50 P (Panthenol and Propylene Glycol) |

Preparation:

Using a propeller mixer, thoroughly mix the feed substances of Phase A in the order given. Then add Phase B to Phase A. Stir slowly until everything is homogeneous. Thoroughly homogenize Phase C until the pigments are well dispersed. Add Phase C and Phase D to Phase AB and mix thoroughly.

Example 5

Waterproof Mascara

A

| | |
|---|---|
| 46.70 | Dist. water |
| 3.00 | Lutrol E 400 (PEG-8) |
| 0.50 | Xanthan gum |
| q.s. | Preservative |
| 0.10 | Imidazolidinylurea |
| 1.30 | Tetrahydroxypropylethylenediamine |

B

| | |
|---|---|
| 8.00 | Carnauba wax |
| 4.00 | Beeswax |
| 4.00 | Isoeicosane |
| 4.00 | Polyisobutene |
| 5.00 | Stearic acid |
| 1.00 | Glyceryl stearate |
| q.s. | Preservative |
| 2.00 | Benzyl laurate |

C

| | |
|---|---|
| 10.00 | Iron oxide/Al Powder/Silicone dioxide (e.g. Sicopearl Fantastico Gold ™ from BASF) |

E

| | |
|---|---|
| 8.00 | Polyurethane-1 |
| 2.00 | Dispersion according to the invention |

Preparation:

Heat Phase A and Phase B separately from one another to 85° C. Maintain the temperature and add Phase C to Phase A and homogenize until the pigments are uniformly dispersed. Add Phase B to Phase AC and homogenize for 2-3 minutes. Then add Phase E and stir slowly. Allow everything to cool to room temperature.

Example 6

Sunscreen Gel

Phase A

| | |
|---|---|
| 1.00 | PEG-40 hydrogenated castor oil |
| 8.00 | Octyl methoxycinnamate (Uvinul MC 80 ™ from BASF) |
| 5.00 | Octocrylene (Uvinul N 539 ™ from BASF) |
| 0.80 | Octyltriazone (Uvinul T 150 ™ from BASF) |
| 2.00 | Butylmethoxydibenzoylmethane (Uvinul BMBM ™ from BASF) |
| 2.00 | Tocopheryl acetate |
| q.s. | Perfume oil |

Phase B

| | |
|---|---|
| 2.50 | Dispersion according to the invention |
| 0.30 | Acrylate/$C_{10-30}$ alkyl acrylate copolymer |
| 0.20 | Carbomer |
| 5.00 | Glycerol |
| 0.20 | Disodium EDTA |
| q.s. | Preservative |
| 72.80 | Dist. water |

Phase C

| | |
|---|---|
| 0.20 | Sodium hydroxide |

Preparation:

Mix the components of Phase A. Allow Phase B to swell and stir into Phase A with homogenization. Neutralize with Phase C and homogenize again.

Example 7

Sunscreen Emulsion with $TiO_2$ and $ZnO_2$

Phase A

| | |
|---|---|
| 6.00 | PEG-7 hydrogenated castor oil |
| 2.00 | PEG-45/Dodecyl glycol copolymer |
| 3.00 | Isopropyl myristate |
| 8.00 | Jojoba oil (*Buxus chinensis*) |
| 4.00 | Octyl methoxycinnamate (Uvinul MC 80) |
| 2.00 | 4-Methylbenzylidenecamphor (Uvinul MBC 95) |
| 3.00 | Titanium dioxide, Dimethicone |
| 1.00 | Dimethicone |
| 5.00 | Zinc oxide, Dimethicone |

Phase B

| | |
|---|---|
| 2.00 | Dispersion according to the invention |
| 0.20 | Disodium EDTA |
| 5.00 | Glycerol |
| q.s. | Preservative |
| 58.80 | Dist. water |

Phase C

| | |
|---|---|
| q.s. | Perfume oil |

Preparation:

Heat Phases A and B separately to about 85° C. Stir Phase B into Phase A and homogenize. Cool to about 40° C., add Phase C and briefly homogenize again.

Example 8

Sunscreen Lotion

Phase A

| | |
|---|---|
| 6.00 | Octyl methoxycinnamate (Uvinul MC 80 ™ from BASF) |
| 2.50 | 4-Methylbenzylidenecamphor (Uvinul MBC 95 ™ from BASF) |

-continued

| | |
|---|---|
| 1.00 | Octyltriazone (Uvinul T 150 ™ from BASF) |
| 2.00 | Butylmethoxydibenzoylmethane (Uvinul BMBM ™ from BASF) |
| 2.00 | PVP/Hexadecene copolymer |
| 5.00 | PPG-3 myristyl ether |
| 0.50 | Dimethicone |
| 0.10 | BHT, ascorbyl palmitate, citric acid, glyceryl stearate, Propylene glycol |
| 2.00 | Cetyl alcohol |
| 2.00 | Potassium cetyl phosphate |
| | Phase B |
| 2.50 | Dispersion according to the invention |
| 5.00 | Propylene glycol |
| 0.20 | Disodium EDTA |
| q.s. | Preservative |
| 63.92 | Dist. water |
| | Phase C |
| 5.00 | Mineral oil |
| 0.20 | Carbomer |
| | Phase D |
| 0.08 | Sodium hydroxide |
| | Phase E |
| q.s. | Perfume oil |

Preparation:

Heat Phases A and B separately to about 80° C. Stir Phase B into Phase A with homogenization, and briefly after-homogenize. Make Phase C into a paste, stir into Phase AB, neutralize with Phase D and after-homogenize. Cool to about 40° C., add Phase E, homogenize again.

Example 9

Peelable Face Mask

| | |
|---|---|
| | Phase A |
| 57.10 | Dist. water |
| 6.00 | Polyvinyl alcohol |
| 5.00 | Propylene glycol |
| | Phase B |
| 20.00 | Alcohol |
| 4.00 | PEG-32 |
| q.s | Perfume oil |
| | Phase C |
| 5.00 | Polyquaternium-44 |
| 2.70 | Dispersion according to the invention |
| 0.20 | Allantoin |

Preparation:

Heat Phase A to at least 90° C. and stir until dissolved. Dissolve Phase B at 50° C. and stir into Phase A. Make up the loss of ethanol at about 35° C. Add Phase C and stir in.

Example 10

Face Mask

| | |
|---|---|
| | Phase A |
| 3.00 | Ceteareth-6 |
| 1.50 | Ceteareth-25 |
| 5.00 | Cetearyl alcohol |
| 6.00 | Cetearyl octanoate |

-continued

| | |
|---|---|
| 6.00 | Mineral oil |
| 0.20 | Bisabolol |
| 3.00 | Glyceryl stearate |
| | Phase B |
| 2.00 | Propylene glycol |
| 5.00 | Panthenol |
| 2.80 | Dispersion according to the invention |
| q.s. | Preservative |
| 65.00 | Dist. water |
| | Phase C |
| q.s. | Perfume oil |
| 0.50 | Tocopheryl acetate |

Preparation:

Heat Phases A and B separately to about 80° C. Stir Phase B into Phase A with homogenization, briefly after-homogenize. Cool to about 40° C., add Phase C, homogenize again.

Example 11

Body Lotion Foam

| | |
|---|---|
| | Phase A |
| 1.50 | Ceteareth-25 |
| 1.50 | Ceteareth-6 |
| 4.00 | Cetearyl alcohol |
| 10.00 | Cetearyl octanoate |
| 1.00 | Dimethicone |
| | Phase B |
| 3.00 | Dispersion according to the invention |
| 2.00 | Panthenol |
| 2.50 | Propylene glycol |
| q.s. | Preservative |
| 74.50 | Dist. water |
| | Phase C |
| q.s. | Perfume oil |

Preparation:

Heat Phases A and B separately to about 80° C. Stir Phase B into Phase A and homogenize. Cool to about 40° C., add Phase C and briefly homogenize again. Bottling: 90% active ingredient and 10% Propane/Butane at 3.5 bar (20° C.).

Example 12

Face Tonic for Dry and Sensitive Skin

| | |
|---|---|
| | Phase A |
| 2.50 | PEG-40 hydrogenated castor oil |
| q.s. | Perfume oil |
| 0.40 | Bisabolol |
| | Phase B |
| 3.00 | Glycerol |
| 1.00 | Hydroxyethylcetyldimonium phosphate |
| 5.00 | Witch hazel distillate (*Hamamelis virginiana*) |
| 0.50 | Panthenol |
| 0.50 | Dispersion according to the invention |
| q.s. | Preservative |
| 87.60 | Dist. water |

Preparation:
Dissolve Phase A until clear. Stir Phase B into Phase A.

Example 13

Face Washing Paste with Peeling Effect

| Phase A | |
|---|---|
| 70.00 | Dist. water |
| 3.00 | Dispersion according to the invention |
| 1.50 | Carbomer |
| q.s. | Preservative |
| Phase B | |
| q.s. | Perfume oil |
| 7.00 | Hydrogenated potassium cocoyl protein |
| 4.00 | Cocamidopropylbetaine |
| Phase C | |
| 1.50 | Triethanolamine |
| Phase D | |
| 13.00 | Polyethylene (Luwax A ™ from BASF) |

Preparation:
Allow Phase A to swell. Dissolve Phase B until clear. Stir Phase B into Phase A. Neutralize with Phase C. Then stir in Phase D.

| Face Soap | |
|---|---|
| Phase A | |
| | Potassium cocoate |
| | Disodium cocoamphodiacetate |
| 2.00 | Lauramide DEA |
| | Glycol stearate |
| 2.00 | Dispersion according to the invention |
| 50.00 | Dist. water |
| q.s. | Citric acid |
| Phase B | |
| q.s. | Preservative |
| q.s. | Perfume oil |

Preparation:
Heat Phase A to 70° C. with stirring until everything is homogeneous, pH to 7.0-7.5 with citric acid, allow everything to cool to 50° C. and add Phase B.

Example 14

O/W Type Face Cleansing Milk

| Phase A | |
|---|---|
| 1.50 | Ceteareth-6 |
| 1.50 | Ceteareth-25 |
| 2.00 | Glyceryl stearate |
| 2.00 | Cetyl alcohol |
| 10.00 | Mineral oil |
| Phase B | |
| 5.00 | Propylene glycol |
| q.s. | Preservative |
| 1.00 | Dispersion according to the invention |
| 66.30 | Dist. water |

-continued

| Phase C | |
|---|---|
| 0.20 | Carbomer |
| 10.00 | Cetearyl octanoate |
| Phase D | |
| 0.40 | Tetrahydroxypropylethylenediamine |
| Phase E | |
| q.s. | Perfume oil |
| 0.10 | Bisabolol |

Preparation:
Heat Phases A and B separately to about 80° C. Stir Phase B into Phase A with homogenization, briefly after-homogenize. Make Phase C into a paste, stir into Phase AB, neutralize with Phase D and after-homogenize. Cool to about 40° C., add Phase E, homogenize again.

Example 15

Transparent Soap

| | |
|---|---|
| 4.20 | Sodium hydroxide |
| 3.60 | Dist. water |
| 2.00 | Dispersion according to the invention |
| 22.60 | Propylene glycol |
| 18.70 | Glycerol |
| 5.20 | Cocoamide DEA |
| 10.40 | Cocamine oxide |
| 4.20 | Sodium lauryl sulfate |
| 7.30 | Myristic acid |
| 16.60 | Stearic acid |
| 5.20 | Tocopherol |

Preparation:
Mix all of the ingredients. Melt the mixture at 85° C. until clear. Immediately pour out into the mold.

Example 16

Peeling Cream, O/W Type

| Phase A | |
|---|---|
| 3.00 | Ceteareth-6 |
| 1.50 | Ceteareth-25 |
| 3.00 | Glyceryl stearate |
| 5.00 | Cetearyl alcohol, sodium cetearyl sulfate |
| 6.00 | Cetearyl octanoate |
| 6.00 | Mineral oil |
| 0.20 | Bisabolol |
| Phase B | |
| 2.00 | Propylene glycol |
| 0.10 | Disodium EDTA |
| 3.00 | Dispersion according to the invention |
| q.s. | Preservative |
| 59.70 | Dist. water |
| Phase C | |
| 0.50 | Tocopheryl acetate |
| q.s. | Perfume oil |
| Phase D | |
| 10.00 | Polyethylene |

Preparation:

Heat Phases A and B separately to about 80° C. Stir Phase B into Phase A and homogenize. Cool to about 40° C., add Phase C and briefly homogenize again. Then stir in Phase D.

Example 17

Shaving Foam

| | |
|---|---|
| 6.00 | Ceteareth-25 |
| 5.00 | Poloxamer 407 |
| 52.00 | Dist. water |
| 1.00 | Triethanolamine |
| 5.00 | Propylene glycol |
| 1.00 | PEG-75 lanolin oil |
| 5.00 | Dispersion according to the invention |
| q.s. | Preservative |
| q.s. | Perfume oil |
| 25.00 | Sodium laureth sulfate |

Preparation:

Weigh everything together, then stir until dissolved. Bottling: 90 parts of active substance and 10 parts of propane/butane mixture 25:75.

Example 18

After Shave Balsam

| Phase A | |
|---|---|
| 0.25 | Acrylate/$C_{10-30}$ alkyl acrylate copolymer |
| 1.50 | Tocopheryl acetate |
| 0.20 | Bisabolol |
| 10.00 | Caprylic/Capric triglyceride |
| q.s. | Perfume oil |
| 1.00 | PEG-40 hydrogenated castor oil |
| Phase B | |
| 1.00 | Panthenol |
| 15.00 | Alcohol |
| 5.00 | Glycerol |
| 0.05 | Hydroxyethylcellulose |
| 1.92 | Dispersion according to the invention |
| 64.00 | Dist. water |
| Phase C | |
| 0.08 | Sodium hydroxide |

Preparation:

Mix the components of Phase A. Stir Phase B into Phase A with homogenization, briefly after-homogenize. Neutralize with Phase C and homogenize again.

Example 19

Body Care Cream

| Phase A | |
|---|---|
| 2.00 | Ceteareth-6 |
| 2.00 | Ceteareth-25 |
| 2.00 | Cetearyl alcohol |
| 3.00 | Glyceryl stearate SE |
| 5.00 | Mineral oil |
| 4.00 | Jojoba oil (*Buxus chinensis*) |
| 3.00 | Cetearyl octanoate |
| 1.00 | Dimethicone |
| 3.00 | Mineral oil, Lanolin alcohol |
| Phase B | |
| 5.00 | Propylene glycol |
| 0.50 | Veegum |
| 1.00 | Panthenol |
| 1.70 | Dispersion according to the invention |
| 6.00 | Polyquaternium-44 |
| q.s. | Preservative |
| 60.80 | Dist. water |
| Phase C | |
| q.s. | Perfume oil |

Preparation:

Heat Phases A and B separately to about 80° C. Homogenize Phase B.

Stir Phase B into Phase A with homogenization, briefly after-homogenize.

Cool to about 40° C., add Phase C and briefly homogenize again.

Example 20

Toothpaste

| Phase A | |
|---|---|
| 34.79 | Dist. water |
| 3.00 | Dispersion according to the invention |
| 0.30 | Preservative |
| 20.00 | Glycerol |
| 0.76 | Sodium monofluorophosphate |
| Phase B | |
| 1.20 | Sodium carboxymethylcellulose |
| Phase C | |
| 0.80 | Aroma oil |
| 0.06 | Saccharin |
| 0.10 | Preservative |
| 0.05 | Bisabolol |
| 1.00 | Panthenol |
| 0.50 | Tocopheryl acetate |
| 2.80 | Silicon dioxide |
| 1.00 | Sodium lauryl sulfate |
| 7.90 | Dicalcium phosphate anhydrous |
| 25.29 | Dicalcium phosphate dihydrate |
| 0.45 | Titanium dioxide |

Preparation:

Dissolve Phase A. Sprinkle Phase B into Phase A and dissolve. Add Phase C and leave to stir under reduced pressure at RT for about 45 min.

Example 21

Mouthwash

| Phase A | |
|---|---|
| 2.00 | Aroma oil |
| 4.00 | PEG-40 hydrogenated castor oil |
| 1.00 | Bisabolol |
| 30.00 | Alcohol |
| Phase B | |
| 0.20 | Saccharin |
| 5.00 | Glycerol |

-continued

| | |
|---|---|
| q.s. | Preservative |
| 5.00 | Poloxamer 407 |
| 0.5 | Dispersion according to the invention |
| 52.30 | Dist. water |

Preparation:

Dissolve Phase A and Phase B separately until clear. Stir Phase B into Phase A.

Example 22

Prosthesis Adhesive

| | Phase A |
|---|---|
| 0.20 | Bisabolol |
| 1.00 | Beta-carotene |
| q.s. | Aroma oil |
| 20.00 | Cetearyl octanoate |
| 5.00 | Silicon dioxide |
| 33.80 | Mineral oil |
| | Phase B |
| 5.00 | Dispersion according to the invention |
| 35.00 | PVP (20% strength solution in water) |

Preparation:

Thoroughly mix Phase A. Stir Phase B into Phase A.

Example 23

Skincare Cream, O/W Type

| | Phase A |
|---|---|
| 8.00 | Cetearyl alcohol |
| 2.00 | Ceteareth-6 |
| 2.00 | Ceteareth-25 |
| 10.00 | Mineral oil |
| 5.00 | Cetearyl octanoate |
| 5.00 | Dimethicone |
| | Phase B |
| 3.00 | Dispersion according to the invention. |
| 2.00 | Panthenol, Propylene glycol |
| q.s. | Preservative |
| 63.00 | Dist. water |
| | Phase C |
| q.s. | Perfume oil |

Preparation:

Heat Phase A and B separately to about 80° C. Stir Phase B into Phase A with homogenization, briefly after-homogenize. Cool to about 40° C., add Phase C, homogenize again.

Example 24

Skincare Cream, W/O Type

| | Phase A |
|---|---|
| 6.00 | PEG-7 hydrogenated castor oil |
| 8.00 | Cetearyl octanoate |
| 5.00 | Isopropyl myristate |
| 15.00 | Mineral oil |

-continued

| | |
|---|---|
| 2.00 | PEG-45/dodecyl glycol copolymer |
| 0.50 | Magnesium stearate |
| 0.50 | Aluminum stearate |
| | Phase B |
| 3.00 | Glycerol |
| 3.30 | Dispersion according to the invention |
| 0.70 | Magnesium sulfate |
| 2.00 | Panthenol |
| q.s. | Preservative |
| 48.00 | Dist. water |
| | Phase C |
| 1.00 | Tocopherol |
| 5.00 | Tocopheryl acetate |
| q.s. | Perfume oil |

Preparation:

Heat Phases A and B separately to about 80° C. Stir Phase B into Phase A and homogenize. Cool to about 40° C., add Phase C and briefly homogenize again.

Example 25

Lip Care Cream

| | Phase A |
|---|---|
| 10.00 | Cetearyl octanoate |
| 5.00 | Polybutene |
| | Phase B |
| 0.10 | Carbomer |
| | Phase C |
| 2.00 | Ceteareth-6 |
| 2.00 | Ceteareth-25 |
| 2.00 | Glyceryl stearate |
| 2.00 | Cetyl alcohol |
| 1.00 | Dimethicone |
| 1.00 | Benzophenone-3 |
| 0.20 | Bisabolol |
| 6.00 | Mineral oil |
| | Phase D |
| 8.00 | Dispersion according to the invention |
| 3.00 | Panthenol |
| 3.00 | Propylene glycol |
| q.s. | Preservative |
| 54.00 | Dist. water |
| | Phase E |
| 0.10 | Triethanolamine |
| | Phase F |
| 0.50 | Tocopheryl acetate |
| 0.10 | Tocopherol |
| q.s. | Perfume oil |

Preparation:

Dissolve Phase A until clear. Add Phase B and homogenize. Add Phase C and melt at 80° C. Heat Phase D to 80° C. Add Phase D to Phase ABC and homogenize. Cool to about 40° C., add Phase E and Phase F, homogenize again.

Example 26

Glossy Lipstick

| | Phase A |
|---|---|
| 5.30 | Candelilla wax (*Euphorbia cerifera*) |
| 1.10 | Beeswax |
| 1.10 | Microcrystalline wax |
| 2.00 | Cetyl palmitate |
| 3.30 | Mineral oil |
| 2.40 | Castor oil, glyceryl ricinoleate, octyldodecanol, carnauba wax, Candelilla wax, |
| 0.40 | Bisabolol |
| 16.00 | Cetearyl octanoate |
| 2.00 | Hydrogenated cocoglycerides |
| q.s. | Preservative |
| 1.00 | Dispersion according to the invention |
| 60.10 | Castor oil (*Ricinus communis*) |
| 0.50 | Tocopheryl acetate |
| | Phase B |
| 0.80 | C.I. 14 720: 1, Acid Red 14 Aluminum Lake |
| | Phase C |
| 4.00 | Mica, titanium dioxide |

Preparation:
Weigh in the components of Phase A and melt. Incorporate Phase B until homogeneous. Add Phase C and stir in. Cool to room temperature with stirring.

Example 26

Shower Gel

| | |
|---|---|
| 50.00 | Sodium laureth sulfate, magnesium laureth sulfate, sodium laureth-8 sulfate, magnesium laureth-8 |
| 1.00 | Cocoamide DEA |
| 4.00 | Dispersion according to the invention |
| 2.00 | Sodium laureth sulfate, glycol distearate, cocamide MEA, laureth-10 |
| q.s. | Preservative |
| q.s. | Perfume oil |
| 2.00 | Sodium chloride |
| 41.00 | Aqua demin. |

Preparation:
Weigh everything together, stir until dissolved.

Example 27

Shower Gel

| | |
|---|---|
| 30.00 | Sodium laureth sulfate |
| 6.00 | Sodium cocoamphodiacetate |
| 6.00 | Cocamidopropylbetaine |
| 3.00 | Sodium laureth sulfate, glycol distearate, cocamide MEA, laureth-10 |
| 7.70 | Polyquaternium-44 |
| 1.50 | Dispersion according to the invention |
| 1.00 | Panthenol |
| q.s. | Preservative |
| q.s. | Perfume oil |
| q.s. | Citric acid |
| 0.50 | Sodium chloride |
| 44.30 | Aqua demin. |

Preparation:
Weigh in the components of Phase A and dissolve. Adjust the pH to 6-7.

Example 28

Clear Shower Gel

| | |
|---|---|
| 40.00 | Sodium laureth sulfate |
| 5.00 | Decyl glucoside |
| 5.00 | Cocamidopropylbetaine |
| 0.50 | Polyquaternium-10 |
| 2.20 | Dispersion according to the invention |
| 1.00 | Panthenol |
| q.s. | Perfume oil |
| q.s. | Preservative |
| q.s. | Citric acid |
| 2.00 | Sodium chloride |
| 44.30 | Aqua demin. |

Preparation:
Weigh in the components of Phase A and dissolve until clear.

Example 29

Shower Bath

| | A |
|---|---|
| 40.00 | Sodium laureth sulfate |
| 5.00 | Sodium C12-15 pareth-15 sulfonate |
| 5.00 | Decyl glucoside |
| q.s. | Perfume oil |
| 0.10 | Phytantriol |
| | B |
| 43.60 | Aqua demin. |
| 0.1 | Guar hydroxypropyl trimonium chloride |
| 2.20 | Dispersion according to the invention |
| 1.00 | Panthenol |
| q.s. | Preservative |
| 1.00 | Laureth-3 |
| q.s. | Citric acid |
| 2.00 | Sodium chloride |

Preparation:
Mix the components of Phase A. Add the components of Phase B one after the other and mix. Adjust the pH to 6-7.

Example 30

Liquid Soap

| | A |
|---|---|
| 44.06 | Aqua demin. |
| 0.34 | Aminomethylpropanol |
| 3.40 | Acrylate Copolymer |
| | B |
| 40.00 | Sodium laureth sulfate |
| 10.00 | Cocamidopropylbetaine |
| 0.20 | Dispersion according to the invention |
| q.s. | Perfume oil |
| q.s. | Preservative |
| 2.00 | Sodium chloride |

Preparation:

Weigh in the components of Phase A and dissolve until clear. Add the components of Phase B one after the other and mix.

Example 31

Liquid Foot Bath

| | A |
|---|---|
| 1.00 | Nonoxynol-14 |
| 0.10 | Bisabolol |
| 1.00 | Pine oil (Pinus sylvestris) |
| | B |
| 5.00 | PEG-8 |
| 1.20 | Dispersion according to the invention |
| 0.50 | Triclosan |
| 30.00 | Sodium laureth sulfate |
| 3.00 | Polyquaternium-16 |
| 58.20 | Aqua demin. |
| q.s. | C.I. 19 140 + C.I. 42 051 |

Preparation:

Solubilize Phase A. Mix Phase B.

Example 32

Freshening Gel

| | A |
|---|---|
| 0.60 | Carbomer |
| 45.40 | Aqua demin. |
| | B |
| 0.50 | Bisabolol |
| 0.50 | Farnesol |
| q.s. | Perfume oil |
| 5.00 | PEG-40 hydrogenated castor oil |
| 0.50 | Dispersion according to the invention |
| 1.00 | Tetrahydroxypropylethylenediamine |
| 1.50 | Menthol |
| 45.00 | Alcohol |
| q.s. | C.I. 74 180, Direct Blue 86 |

Preparation:

Allow Phase A to swell. Dissolve Phase B. Stir Phase B into Phase A.

Example 33

Roll-on Antiperspirant

| | A |
|---|---|
| 0.40 | Hydroxyethylcellulose |
| 50.00 | Aqua demin. |
| | B |
| 25.00 | Alcohol |
| 0.10 | Bisabolol |
| 0.30 | Farnesol |
| 2.00 | PEG-40 hydrogenated castor oil |
| q.s. | Perfume oil |

| | C |
|---|---|
| 5.00 | Aluminum chlorohydrate |
| 3.00 | Propylene glycol |
| 3.00 | Dimethicone copolyol |
| 3.00 | Polyquaternium-16 |
| 1.20 | Dispersion according to the invention |
| 7.00 | Aqua demin. |

Preparation:

Allow Phase A to swell. Dissolve Phase B and Phase C separately. Stir Phase A and Phase B into Phase C.

Example 34

Transparent Deodorant Stick

| 5.00 | Sodium stearate |
|---|---|
| 0.50 | Triclosan |
| 3.00 | Ceteareth-25 |
| 20.00 | Glycerol |
| 0.50 | Dispersion according to the invention |
| q.s. | Perfume oil |
| 60.00 | Propylene glycol |
| 0.20 | Bisabolol |
| 10.80 | Aqua demin. |

Preparation:

Weigh Phase A together, melt and homogenize. Then pour into the mold.

Example 35

Water-Soluble Bath Oil

| 15.00 | Cetearyl octanoate |
|---|---|
| 15.00 | Caprylic/capric triglyceride |
| 1.00 | Panthenol, propylene glycol |
| 0.10 | Bisabolol |
| 2.00 | Tocopheryl acetate |
| 2.00 | Retinyl palmitate |
| 0.10 | Tocopherol |
| 37.00 | PEG-7 glyceryl cocoate |
| 0.40 | Dispersion according to the invention |
| 3.80 | Aqua demin. |
| q.s. | Perfume oil |
| 23.60 | PEG-40 hydrogenated castor oil |

Preparation:

Mix and stir until everything is dissolved to form a clear solution.

Example 36

Daycare Aerosol

| | A |
|---|---|
| 4.00 | Ethylhexyl methoxycinnamate |
| 1.50 | Octocrylene |
| 9.00 | Caprylic/capric triglyceride |
| 5.00 | Simmondsia chinensis (jojoba) seed oil |
| 1.50 | Cyclomethicone |
| 3.00 | Hydrogenated cocoglycerides |
| 1.00 | PVP/Hexadecene copolymer |
| 1.00 | Ceteareth-6, stearyl alcohol |

-continued

| | B |
|---|---|
| 5.00 | Zinc oxide |
| | C |
| 2.00 | Ceteareth-25 |
| 1.20 | Panthenol |
| 0.20 | Sodium ascorbyl phosphate |
| 0.30 | Imidazolidinylurea |
| 0.10 | Disodium EDTA |
| 1.50 | Dispersion according to the invention |
| 62.67 | Aqua demin. |
| | D |
| 0.50 | Tocopheryl acetate |
| 0.20 | Bisabolol |
| 0.33 | Caprylic/capric triglyceride, retinol |
| q.s. | Perfume oil |

Preparation:

Heat Phase A to 80° C. Dissolve Phase A until clear. Incorporate Phase B and homogenize. Add Phase C, heat to 80° C., melt and homogenize. Cool to about 40° C. with stirring, add to Phase D and briefly homogenize. Bottle 90% active ingredient solution: 10% propane/butane with 3.5 bar (20° C.).

Example 37

Moisturizing Cream

| | A |
|---|---|
| 3.00 | *Vitis vinifera* (grape) seed oil |
| 1.00 | Cyclopentasiloxane, cyclohexasiloxane |
| 1.50 | Cyclomethicone |
| 2.00 | Soybean oil (*glycine soya*) |
| 2.00 | Ethylhexyl methoxycinnamate |
| 1.00 | Uvinul A Plus (BASF) |
| 1.00 | Hydrogenated Lecithin |
| 1.00 | Cholesterol |
| 2.00 | PEG-40 hydrogenated castor oil |
| 5.00 | Cetearyl octanoate |
| 5.00 | Caprylic/capric triglyceride |
| | B |
| 3.00 | Caprylic/capric triglyceride, acrylate copolymer |
| | C |
| 3.00 | Dispersion according to the invention |
| 0.50 | Cocotrimonium methosulfate |
| 2.00 | Panthenol, propylene glycol |
| 3.00 | Glycerol |
| 0.10 | Disodium EDTA |
| 60.30 | Aqua demin. |
| | D |
| 0.30 | Perfume |
| 0.30 | DMDM hydantoin |
| 1.00 | Tocopheryl acetate |
| 2.00 | Tocopherol |

Preparation:

Heat Phase A to 80° C. Stir Phase B into Phase A. Heat Phase C to about 80° C. and stir into Phase A+B with homogenization. Cool to about 40° C. with stirring, add Phase D and briefly homogenize.

Example 38

Aerosol Hair Foam

| | A |
|---|---|
| 2.00 | Cocotrimonium methosulfate |
| 0.20 | Perfume oil |
| | B |
| 63.90 | Aqua demin. |
| 6.70 | Dispersion according to the invention |
| 0.50 | Acrylates copolymer |
| 0.10 | Aminomethylpropanol |
| 0.20 | Ceteareth-25 |
| 0.20 | Trimethylsilylamodimethicone, trideceth-10, cetrimonium chloride |
| 0.10 | PEG-25 PABA |
| 0.20 | Hydroxyethylcellulose |
| 0.20 | PEG-8 |
| 0.20 | Panthenol |
| 15.00 | Alcohol |
| | C |
| 10.00 | Propane/butane 3.5 bar (20° C.) |

Preparation:

Mix Phases A and B and bottle with propellant gas.

Example 39

Pump Mousse

| | A |
|---|---|
| 2.00 | Cocotrimonium methosulfate |
| q.s. | Perfume oil |
| | C |
| 86.30 | Aqua demin. |
| 7.00 | Polyquaternium-46 |
| 3.00 | Dispersion according to the invention |
| 0.50 | PEG-8 |
| 1.00 | Panthenol |
| q.s. | Preservative |
| 0.20 | PEG-25 PABA |

Preparation:

Mix the components of Phase A. Add the components of Phase B one after the other and dissolve until clear.

Example 40

Aerosol Foam

| 15.00 | Dispersion according to the invention |
|---|---|
| 5.00 | PVP/VA copolymer |
| 0.50 | Hydroxyethylcetyldimonium phosphate |
| 0.20 | Ceteareth-25 |
| 0.40 | Perfume oil PC 910.781/Cremophor |
| 68.90 | Aqua demin. |
| q.s. | Preservative |
| 10.00 | Propane/butane 3.5 bar (20° C.) |

Preparation:

Weigh everything together, stir until dissolved, then bottle.

Example 41

Color Styling Mousse

| | A |
|---|---|
| 2.00 | Cocotrimonium methosulfate |
| q.s. | Perfume oil |
| | B |
| 6.70 | Dispersion according to the invention |
| 0.50 | Acrylate copolymer |
| 0.10 | Aminomethylpropanol |
| 0.20 | Ceteareth-25 |
| 0.20 | Panthenol |
| 0.20 | Hydroxyethylcellulose |
| 10.00 | Alcohol |
| 69.97 | Aqua demin. |
| 0.08 | C.I. 12245, Basic Red 76 |
| 0.05 | C.I. 42510, Basic Violet 14 |
| | C |
| 10.00 | Propane/Butane 3.5 bar (20° C.) |

Preparation:

Weigh everything together, stir until dissolved, then bottle. Only suitable for dark blonde and brown hair!

Example 42

Aerosol Hair Foam

| | A |
|---|---|
| 0.20 | Perfume oil |
| 2.00 | Cocotrimonium methosulfate |
| | B |
| 69.90 | Aqua demin. |
| 14.70 | Polyurethane-1 |
| 2.00 | Dispersion according to the invention |
| 0.50 | PEG-25 PABA |
| 0.20 | Amodimethicone, tallow trimonium chloride, nonoxynol-10 |
| q.s. | Preservative |
| 0.50 | Ceteareth-25 |
| | C |
| 10.00 | Propane/butane 3.5 bar (20° C.) |

Preparation:

Mix Phase A. Add the components of Phase B one after the other and dissolve. Bottle with Phase C.

Example 43

Pump Hair Foam

| | A |
|---|---|
| 1.50 | Cocotrimonium methosulfate |
| q.s. | Perfume oil |
| | B |
| 2.00 | Dispersion according to the invention |
| 94.04 | Aqua demin. |

-continued

| | C |
|---|---|
| 0.46 | Aminomethylpropanol |
| 4.00 | PEG/PPG-25/25 dimethicone/acrylates copolymer |
| q.s. | Preservative |

Preparation:

Mix Phase A. Stir Phase B into Phase A. Add Phase C and stir until dissolved.

Example 44

Hair Styling Gel

| | A |
|---|---|
| 0.50 | Carbomer |
| 87.60 | Aqua demin. |
| | B |
| 0.70 | Triethanolamine |
| | C |
| 6.00 | Dispersion according to the invention |
| 5.00 | PVP (Luviskol K30 or Luviskol K90) |
| q.s. | Perfume oil |
| q.s. | PEG-40 hydrogenated castor oil |
| q.s. | Preservative |
| 0.10 | Tocopheryl acetate |

Preparation:

Allow Phase A to swell and neutralize with Phase B. Dissolve Phase C and stir into Phase A+B.

Example 45

Hair Styling Gel

| | A |
|---|---|
| 0.50 | Carbomer |
| 87.60 | Aqua demin. |
| | B |
| 0.90 | Tetrahydroxypropylethylenediamine |
| | C |
| 2.00 | Dispersion according to the invention |
| 9.00 | VP/VA copolymer (Luviskol VA64W; BASF) |
| q.s. | Perfume oil |
| q.s. | PEG-40 hydrogenated castor oil |
| q.s. | Preservative |
| 0.10 | Propylene glycol |

Preparation:

Allow Phase A to swell and neutralize with Phase B. Dissolve Phase C and stir into Phase A+B.

Example 46

Hair Styling Gel

| 2.00 | Dispersion according to the invention |
|---|---|
| 6.00 | Modified corn starch (Amaze, National Starch) |
| 0.50 | Chitosan |
| q.s. | Perfume oil |

Example 47

Hair Styling Gel

| | |
|---|---|
| 8.00 | Dispersion according to the invention |
| 5.00 | VP/DMAPA acrylate copolymers (ISP: Styleze CC-10) |
| 0.05 | Aminomethylpropanol |
| 84.85 | Aqua demin. |
| q.s. | Perfume oil |
| q.s. | PEG-40 hydrogenated castor oil |
| 0.10 | Dimethicone copolyol |
| 0.10 | Preservative |
| 2.00 | Hydroxypropylcellulose |

Preparation:

Mix all of the components until they are homogeneous.

Example 48

Hair Styling Gel

| | |
|---|---|
| 6.00 | Dispersion according to the invention |
| 1.00 | VP/acrylate/lauryl methacrylate copolymers (ISP: Styleze 2000) |
| 0.26 | Aminomethyl propanol |
| 90.64 | Aqua demin. |
| q.s. | Perfume oil |
| q.s. | Hydrogenated castor oil PEG-40 |
| 0.10 | Sorbitol |
| 0.10 | Preservative |
| 2.00 | Hydroxypropyl guar (Rhodia Inc., N-Hance hydroxypropylguar) |

Preparation:

Mix all of the components until they are homogeneous.

Example 49

Hair Gel

| | |
|---|---|
| A | |
| 0.50 | Carbomer |
| 90.01 | Aqua demin. |
| B | |
| 0.70 | Triethanolamine |
| C | |
| 6.00 | Dispersion according to the invention |
| 2.00 | Acrylate/$C_{1-2}$ succinate/hydroxyacrylate copolymers (Rohm&Haas, Allianz LT-120) |
| 0.19 | Aminomethylpropanol |
| q.s. | Perfume oil |
| q.s. | PEG-40 hydrogenated castor oil |
| 0.10 | PEG-8 |
| 0.10 | Preservative |
| 0.50 | Hydroxyethylcellulose |

Preparation:

Allow Phase A to swell and neutralize with Phase B. Dissolve Phase C and stir into Phase A+B.

Example 50

Hair Gel

| | |
|---|---|
| 7.00 | Dispersion according to the invention |
| 7.00 | Methacrylic acid/sodium acrylamidomethylpropanesulfonate copolymer (Ondeo Nalco, Fixomer A30) |
| 0.70 | Triethanolamine |
| q.s. | Perfume oil |
| q.s. | Hydrogenated castor oil PEG-40 |
| 0.10 | Panthenol |
| 0.10 | Preservative |
| 84.90 | Aqua demin. |
| 1.00 | Polyacrylamide/$C_{13-14}$-isoparaffin/laureth-7 (Seppic, Sepigel 305) |

Preparation:

Mix all of the components until they are homogeneous.

Example 51

Hair Gel

| | |
|---|---|
| A | |
| 0.50 | Carbomer |
| 90.50 | Aqua demin. |
| B | |
| 0.70 | Triethanolamine |
| C | |
| 7.00 | Dispersion according to the invention |
| 1.00 | Polyvinylformamide |
| q.s. | Perfume oil |
| q.s. | PEG-40 hydrogenated castor oil |
| 0.10 | Preservative |
| 0.10 | Ethylhexyl methoxycinnamate |
| 0.10 | PEG-14 dimethicone |

Preparation:

Allow Phase A to swell and neutralize with Phase B. Dissolve Phase C and stir into Phase A+B.

Example 52

Aquawax

| | |
|---|---|
| 10.00 | Dispersion according to the invention |
| q.s. | Perfume oil |
| q.s. | PEG-40 hydrogenated castor oil |
| 0.10 | Diethyl phthalate |
| 0.10 | Cetearyl ethylhexanoate |
| 0.10 | PEG-7 glyceryl cocoate |
| 0.10 | Preservative |
| 87.70 | Aqua demin. |
| 2.00 | Caprylic/capric triglyceride, acrylate copolymer |

-continued

| | |
|---|---|
| q.s. | Hydrogenated castor oil PEG-40 |
| 0.10 | PEG-14 dimethicone |
| 0.10 | Preservative |
| 91.40 | Aqua demin. |

Preparation:

Mix all of the components until they are homogeneous.

Preparation:

Mix everything and homogenize. After-stir for 15 minutes.

Example 53

Rinse-off Conditioner and Repair Treatment

| | A |
|---|---|
| 0.20 | Cetearyl octanoate |
| 0.10 | Phytantriol |
| 2.00 | Hydrogenated castor oil PEG-40 |
| | B |
| q.s. | Perfume oil |
| 2.00 | Cocotrimonium methosulfate |
| | C |
| 77.70 | Aqua demin. |
| | D |
| 2.00 | Polyquaternium-16 |
| 5.00 | Dispersion according to the invention |
| 1.00 | Dimethicone copolyol |
| q.s. | Preservative |
| 10.00 | Alcohol |
| q.s. | Citric acid |

Preparation:

Mix Phases A and B separately. Stir Phase C into Phase B.

Example 54

Hair Treatment

| | A |
|---|---|
| 2.00 | Ceteareth-6, stearyl alcohol |
| 1.00 | Ceteareth-25 |
| 6.00 | Cetearyl alcohol |
| 6.00 | Cetearyl octanoate |
| 0.30 | Phytantriol |
| | B |
| 5.00 | Dispersion according to the invention |
| 0.70 | Guar hydroxypropyltrimonium chloride |
| 5.00 | Propylene glycol |
| 2.00 | Panthenol |
| 0.30 | Imidazolidinylurea |
| 69.00 | Aqua demin. |
| | C |
| 2.00 | Cosi silk soluble |
| 0.20 | Perfume |
| 0.50 | Phenoxyethanol |

Preparation:

Heat Phases A and B separately to about 80° C. Homogenize Phase B.

Example 55

Hair Cocktail

| | A |
|---|---|
| 0.40 | Acrylate/$C_{10-30}$ alkyl acrylate copolymers |
| 2.00 | Dimethicone |
| 3.00 | Cyclomethicone, dimethiconol |
| 2.00 | Phenyl trimethicone |
| 2.00 | Amodimethicone, cetrimonium chloride, trideceth-10 |
| 0.50 | Dimethicone copolyol |
| 1.00 | Macadamia nut oil (ternifolia) |
| 0.50 | Tocopheryl acetate |
| 1.00 | PEG-40 hydrogenated castor oil |
| q.s. | Perfume oil |
| | B |
| 82.84 | Aqua demin. |
| 0.30 | Dispersion according to the invention |
| 0.46 | Aminomethylpropanol |
| 4.00 | PEG/PPG-25/25 dimethicone/acrylate copolymer |

Preparation:

Mix the components of Phase A. Dissolve Phase B. Stir Phase B into Phase A with homogenization.

Example 56

Permanent Wave

| | Waving Solution |
|---|---|
| | A |
| 73.95 | Aqua demin. |
| 0.20 | Cocamidopropylbetaine |
| 0.20 | Polysorbate 20 |
| 1.25 | Polymer according to the invention |
| 0.20 | Disodium EDTA |
| 0.20 | Hydroxyethylcellulose |
| | B |
| 8.00 | Thioglycolic acid |
| | C |
| 11.00 | Ammonium hydroxide |
| | D |
| 5.00 | Ammonium carbonate |

Preparation:

Weigh in the components of Phase A and dissolve until clear. Stir Phase B into Phase A.

Neutralization:

| | A |
|---|---|
| 1.00 | PEG-40 hydrogenated castor oil |
| 0.20 | Perfume oil |
| 93.60 | Aqua demin. |
| | B |
| 0.20 | Cocamidopropylbetaine |
| 0.20 | Ceteareth-25 |
| 2.50 | Dispersion according to the invention |
| q.s. | Preservative |
| | C |
| 2.30 | Hydrogen peroxide |
| | D |
| q.s. | Phosphoric acid |

Preparation:

Solubilize Phase A. Add the components of Phase B one after the other and dissolve until clear.

Example 57

Dark Brown Permanent Hair Color (Oxidation Hair Color)

| A | |
|---|---|
| 50.90 | Aqua demin. |
| 0.20 | Sodium sulfite |
| 0.05 | Disodium EDTA |
| 0.20 | p-Phenylenediamine |
| 0.30 | Resorcinol |
| 0.20 | 4-Amino-2-hydroxytoluene |
| 0.10 | m-Aminophenol |
| 1.50 | Oleyl alcohol |
| 4.50 | Propylene glycol |
| 2.30 | Sodium $C_{12-15}$ pareth-15 sulfonate |
| 20.00 | Oleic acid |
| B | |
| 1.00 | Dispersion according to the invention |
| 13.70 | Ammonium hydroxide |
| 6.00 | i-Propanol |
| q.s. | Perfume |

Preparation:

Solubilize Phase A. Add the components of Phase B one after the other and mix.

| Developer Emulsion (pH: 3-4) | |
|---|---|
| 3.00 | Hexadecyl alcohol |
| 2.00 | Dispersion according to the invention |
| 1.00 | Ceteareth-20 |
| 1.00 | Sodium $C_{12-15}$ pareth-15 sulfonate |
| 6.00 | Hydrogen peroxide |
| 0.50 | Phosphoric acid |
| 0.01 | Acetanilide |
| 86.49 | Aqua demin. |

Preparation:

Add the components one after the other and mix.

Example 58

Pale Brown Semi-Permanent Hair Color

| | |
|---|---|
| 10.00 | Cocodiethanolamide |
| 4.00 | Sodium dodecylbenzylsulfonate, 50% strength |
| 1.00 | Dispersion according to the invention |
| 6.00 | $C_{9-11}$ pareth-3 |
| 2.50 | Sodium lauryl sulfate |
| 0.40 | 2-Nitro-p-phenylenediamine |
| 0.20 | HC Red No. 3 |
| 0.20 | HC Yellow No. 2 |
| 75.70 | Aqua demin. |

Preparation:

Add the components one after the other and mix.

Example 59

Clear Conditioning Shampoo

| A | |
|---|---|
| 15.00 | Cocamidopropylbetaine |
| 10.00 | Disodium cocoamphodiacetate |
| 5.00 | Polysorbate 20 |
| 5.00 | Decyl glucoside |
| q.s. | Perfume |
| q.s. | Preservative |
| 0.1-1.00 | Dispersion according to the invention |
| 2.00 | Laureth-3 |
| ad 100 | Aqua demin. |
| q.s. | Citric acid |
| B | |
| 3.00 | PEG-150 distearate |

Preparation:

Weigh in the components of Phase A and dissolve. Adjust pH to 6-7. Add Phase B and heat to 50° C. Allow to cool to room temperature with stirring.

Example 60

Shampoo

| | |
|---|---|
| 30.00 | Sodium laureth sulfate |
| 6.00 | Sodium cocoamphoacetate |
| 6.00 | Cocamidopropylbetaine |
| 3.00 | Sodium laureth sulfate, glycol distearate, cocamide MEA, laureth-10 |
| 0.10-1.00 | Dispersion according to the invention |
| 2.00 | Dimethicone |
| q.s. | Perfume |
| q.s. | Preservative |
| q.s. | Citric acid |
| 1.00 | Sodium chloride |
| ad 100 | Aqua demin. |

Preparation:

Weigh in components and dissolve. Adjust pH to 6-7.

Example 61

Shampoo

| | |
|---|---|
| 30.00 | Sodium laureth sulfate |
| 6.00 | Sodium cocoamphoacetate |
| 6.00 | Cocamidopropylbetaine |
| 3.00 | Sodium laureth sulfate, glycol Distearate, cocamide MEA, laureth-10 |
| 0.10-1.00 | Dispersion according to the invention |
| 2.00 | Amodimethicone |
| q.s. | Perfume |
| q.s. | Preservative |
| q.s. | Citric acid |
| 1.00 | Sodium chloride |
| ad 100 | Aqua demin. |

Example 62

Shampoo

| | |
|---|---|
| 40.00 | Sodium laureth sulfate |
| 10.00 | Cocamidopropylbetaine |
| 3.00 | Sodium laureth sulfate, glycol distearate, cocamide MEA, laureth-10 |
| 0.10-1.00 | Dispersion according to the invention |
| 2.00 | Dow Corning 3052 |
| q.s. | Perfume |
| q.s. | Preservative |
| q.s. | Citric acid |
| 2.00 | Cocamido DEA |
| ad 100 | Aqua demin. |

Preparation:

Weigh in the components and dissolve. Adjust pH to 6-7.

Example 63

Antidandruff Shampoo

| | |
|---|---|
| 40.00 | Sodium laureth sulfate |
| 10.00 | Cocamidopropylbetaine |
| 10.00 | Disodium laureth sulfosuccinate |
| 2.50 | Sodium laureth sulfate, glycol distearate, cocamide MEA, laureth-10 |
| 0.1-1.0 | Dispersion according to the invention |
| 0.50 | Climbazole |
| q.s. | Perfume |
| q.s. | Preservative |
| 0.50 | Sodium chloride |
| ad 100 | Aqua demin. |

Preparation:

Weigh in components and dissolve. Adjust pH to 6-7.

Example 64

Shampoo

| | |
|---|---|
| 25.00 | Sodium laureth sulfate |
| 5.00 | Cocamidopropylbetaine |
| 2.50 | Sodium laureth sulfate, glycol distearate, cocamide MEA, laureth-10 |
| 0.1-1.0 | Dispersion according to the invention |
| q.s. | Perfume |
| q.s. | Preservative |
| 2.00 | Cocamido DEA |
| ad 100 | Aqua demin. |

Preparation:

Weigh in the components and dissolve. Adjust pH to 6-7.

Example 65

Shampoo

| | |
|---|---|
| 20.00 | Ammonium laureth sulfate |
| 15.00 | Ammonium lauryl sulfate |
| 5.00 | Cocamidopropylbetaine |
| 2.50 | Sodium laureth sulfate, glycol distearate, cocamide MEA, laureth-10 |
| 0.10-1.00 | Dispersion according to the invention |
| q.s. | Perfume |
| q.s. | Preservative |
| 0.50 | Sodium chloride |
| ad 100 | Aqua demin. |

Preparation:

Weigh in components and dissolve. Adjust pH to 6-7.

Example 66

Clear Shower Gel

| | |
|---|---|
| 40.00 | Sodium laureth sulfate |
| 5.00 | Decyl glucoside |
| 5.00 | Cocamidopropylbetaine |
| 0.10-1.00 | Dispersion according to the invention |
| 1.00 | Panthenol |
| q.s. | Perfume |
| q.s. | Preservative |
| q.s. | Citric acid |
| 2.00 | Sodium chloride |
| ad 100 | Aqua demin. |

Preparation:

Weigh in components and dissolve. Adjust pH to 6-7.

Example 67

Shampoo

| | |
|---|---|
| 12.00 | Sodium laureth sulfate |
| 1.50 | Decyl glucoside |
| 2.50 | Cocamidopropylbetaine |
| 5.00 | Cocoglucoside glyceryl oleate |
| 2.00 | Sodium laureth sulfate, glycol distearate, cocamide MEA, laureth-10 |
| 0.10-1.00 | Dispersion according to the invention |
| q.s. | Preservative |
| q.s. | Sunset Yellow C.I. 15 985 |
| q.s. | Perfume |
| 1.00 | Sodium chloride |
| ad 100 | Aqua demin. |

Preparation:

Weigh in components and dissolve. Adjust pH to 6-7.

Example 68

Shampoo

| A | |
|---|---|
| 40.00 | Sodium laureth sulfate |
| 5.00 | Sodium $C_{12-15}$ pareth-15 sulfonate |
| 5.00 | Decyl glucoside |
| q.s. | Perfume |
| 0.10 | Phytantriol |
| B | |
| ad 100 | Aqua demin. |
| 0.10-1.00 | Dispersion according to the invention |
| 1.00 | Panthenol |
| q.s. | Preservative |
| 1.00 | Laureth-3 |
| q.s. | Citric acid |
| 2.00 | Sodium chloride |

Preparation:

Weigh in components of Phase A and dissolve. Adjust pH to 6-7. Add Phase B and mix.

We claim:

1. An aqueous polymer dispersion Pd) obtained by free-radical polymerization of a monomer mixture M) comprising
    a) at least one α,β-ethylenically unsaturated amide-group-containing compound of the formula I

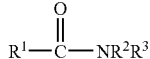

where
    $R^2$ is a group of the formula $CH_2=CH-$ and $R^1$ and $R^3$, independently of one another, are H, alkyl, cycloalkyl, heterocycloalkyl, aryl or hetaryl, or $R^1$ and $R^3$, together with the amide group to which they are bonded, are a lactam with 5 to 8 ring atoms,
    b) at least one free-radically polymerizable crosslinking compound with at least two α,β-ethylenically unsaturated double bonds per molecule,
    c) at least one compound with a free-radically polymerizable α,β-ethylenically unsaturated double bond and at least one cationogenic and/or cationic group per molecule,
    wherein the monomer mixture M) is polymerized in an aqueous medium in the presence of 10 to 90% by weight of at least one polymeric anionic dispersant D) based on the total weight of component a) and the at least one polymeric anionic dispersant D), and
    wherein the at least one polymeric anionic dispersant D) is selected from the group consisting of maleic acid-acrylic acid copolymers and salts thereof, maleic acid-methyl vinyl ether copolymers and salts thereof, maleic acid-olefin copolymers and salts thereof, and maleic anhydride-styrene copolymers.

2. A polymer dispersion as claimed in claim 1, where the monomer mixture M) additionally comprises at least one further monomer d) which is chosen from esters of α,β-ethylenically unsaturated mono- and dicarboxylic acids with $C_1$-$C_{30}$-alkanols and $C_1$-$C_{30}$-alkanediols, amides of α,β-ethylenically unsaturated mono- and dicarboxylic acids with $C_2$-$C_{30}$-amino alcohols which have a primary or secondary amino group, primary amides of α,β-ethylenically unsaturated monocarboxylic acids and N-alkyl and N,N-dialkyl derivatives thereof, esters of vinyl alcohol and allyl alcohol with $C_1$-$C_{30}$-monocarboxylic acids, vinyl ethers, vinyl aromatics, vinyl halides, vinylidene halides, $C_1$-$C_8$-monoolefins, nonaromatic hydrocarbons with at least two conjugated double bonds and mixtures thereof.

3. A polymer dispersion as claimed in claim 1, where the monomer mixture M) additionally comprises at least one compound e) with a free-radically polymerizable α,β-ethylenically unsaturated double bond and an anionogenic and/or anionic group per molecule, with the proviso that the molar proportion of anionogenic and anionic groups in component e) is lower than the molar proportion of cationogenic and cationic groups in component c).

4. A polymer dispersion as claimed in claim 1, where component a) is chosen from N-vinylamides of saturated monocarboxylic acids, N-vinyllactams and mixtures thereof.

5. A polymer dispersion as claimed in claim 1, where component c) is chosen from esters of α,β-ethylenically unsaturated mono- and dicarboxylic acids with amino alcohols, which may be mono- or dialkylated on the amine nitrogen, amides of α,β-ethylenically unsaturated mono- and dicarboxylic acids with diamines which have at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds and mixtures thereof.

6. A polymer dispersion as claimed in claim 5, where component c) comprises vinylimidazole or an acid salt or a quaternization product thereof.

7. A polymer dispersion as claimed in claim 3, where component e) is chosen from monoethylenically unsaturated carboxylic acids, sulfonic acids, phosphonic acids and mixtures thereof.

8. A polymer dispersion as claimed in claim 1, where the at least one polymeric anionic dispersant D) is selected from the group consisting of maleic acid-acrylic acid copolymers and salts thereof.

9. A polymer dispersion as claimed in claim 1, where component a) is used in an amount of from 10 to 90% by weight, based on the total weight of component a) and the dispersant D).

10. A polymer dispersion as claimed in claim 1, where component b) is used in an amount of from 0.0005 to 5% by weight, based on the weight of component a).

11. A polymer dispersion as claimed in claim 1, where component c) is used in an amount of from 1 to 40% by weight, based on the total weight of component a) and the dispersant D).

12. A polymer dispersion as claimed in claim 1, where the polymerization additionally takes place in the presence of at least one regulator.

13. A polymer dispersion as claimed in claim 1, where the pH of the aqueous medium for the polymerization is adjusted to 6 to 8.

14. A polymer dispersion as claimed in claim 1, which has an LT (light transmittance value) of at most 30%.

15. A polymer dispersion as claimed in claim 1, which has an LT (light transmittance value) of at most 5%.

16. A polymer P) obtainable by drying a polymer dispersion Pd), as defined in claim 1.

17. A cosmetic or pharmaceutical composition comprising
    A) at least one polymer dispersion Pd), as defined in claim 1, or a polymer P), as defined in claim 16, and
    B) at least one cosmetically acceptable carrier.

18. A composition as claimed in claim 17, where component B) is chosen from
  i) water,
  ii) water-miscible organic solvents, preferably $C_1$-$C_4$-alkanols,
  iii) oils, fats, waxes,
  iv) esters of $C_6$-$C_{30}$-monocarboxylic acids with mono-, di- or trihydric alcohols which are different from iii),
  v) saturated acyclic and cyclic hydrocarbons,
  vi) fatty acids,
  vii) fatty alcohols
  and mixtures thereof.

19. A composition as claimed in claim 17, further comprising at least one constituent different from component A) which is chosen from cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tinting agents, tanning agents, dyes, pigments, consistency-imparting agents, humectants, refatting agents, collagen, protein hydrolyzates, lipids, antioxidants, antifoams, antistats, emollients and softeners.

20. A composition as claimed in claim 17 in the form of a gel, foam, spray, ointment, cream, emulsion, suspension, lotion, milk or paste.

* * * * *